(12) United States Patent
Fox et al.

(10) Patent No.: US 6,958,151 B2
(45) Date of Patent: Oct. 25, 2005

(54) MINIPROTEIN LIGANDS AND OTHER POLYPEPTIDES AND METHODS FOR MAKING AND USING SAME

(75) Inventors: Robert O. Fox, Galveston, TX (US);
Alan D. Barrett, Galveston, TX (US);
Xiuzhen Fan, Galveston, TX (US);
Michael R. Holbrook, Oklahoma City, O

FIG. 1

Conotoxin GI α    E-CC-NPA-C-GRHYS-C  (SEQ ID NO: 180)

MP-100           R-CC-HPQ-C-KEGKK-C-R (SEQ ID NO: 157)

Crossed;
MP-100C

Nested;
MP-100N

- Cys
- Uncharged
- Basic
- Acidic

FIG. 2

MINIPROTEIN LIGANDS AND OTHER POLYPEPTIDES AND METHODS FOR MAKING AND USING SAME

The present application claims the benefit of U.S. Provisional Patent Application Ser. No. 60/365,020, filed Mar. 15, 2002, which provisional patent application is hereby incorporated by reference.

The present invention was made with the support of the Defense Advanced Research Projects Agency of the Department of Defense Contract No. N65236-97-1-5811 and with the support of the National Institutes of Health Center for Disease Control Contract No. U90/CCU618754. The Federal Government may have certain rights in this invention.

FIELD OF THE INVENTION

The present invention is directed generally to polypeptides and miniprotein ligands and to methods for making and using same.

BACKGROUND OF THE INVENTION

A wide variety of viruses are known to cause infection and other forms of disease in man and other animals.

One group of such viruses is the flaviviruses. The genus *Flavivirus* within the family Flaviviridae consists of approximately 70 viruses. Most of these viruses are transmitted by either mosquito or tick vectors. Several flaviviruses are significant human pathogens, including the four dengue viruses (DEN 1, DEN 2, DEN 3, and DEN 4), yellow fever ("YF"), Japanese encephalitis ("JE"), West Nile ("WN"), and members of the tick-borne encephalitis ("TBE") serocomplex. Mosquitoes transmit dengue fever throughout tropical and subtropical environments worldwide. Mosquito-borne YF virus is found primarily in tropical and subtropical Africa and South America, whereas JE virus is found in Asia and Indonesia. In addition, to the encephalitic members of the TBE serocomplex, three hemorrhagic viruses have been described: Kyasanur Forest disease ("KFD"), Omsk hemorrhagic fever ("OHF"), and Alkhurma viruses that are found in India, Siberia, and Saudi Arabia, respectively. Currently, the National Institute of Allergy and Infectious Diseases of the U.S. National Institutes of Health includes the following flaviviruses in the category A, B, and C lists: dengue, WN, JE, YF, KFD, and members of the tick-borne encephalitis complex, such as Russian spring summer encephalitis ("RSSE"), central European TBE, and OHF.

In the case of dengue, the viruses are transmitted to man by mosquitoes of the genus *Aedes*, primarily *A. aegypti* and *A. albopictus*. The viruses cause an illness manifested by high fever, headache, aching muscles and joints, and rash. Some cases, typically in children, result in a more severe forms of infection, dengue hemorrhagic fever and dengue shock syndrome, marked by severe hemorrhage, vascular permeability, or both, leading to shock. Without diagnosis and prompt medical intervention, the sudden onset and rapid progression of dengue hemorrhagic fever and dengue shock syndrome can be fatal.

Flaviviruses are the most significant group of arthropod-transmitted viruses in terms of global morbidity and mortality with an estimated one hundred million cases of dengue fever occurring annually. With the global increase in population and urbanization, especially throughout the tropics, and the lack of sustained mosquito control measures, the mosquito vectors of flavivirus have distributed throughout the tropics, subtropics, and some temperate areas, bringing the risk of flaviviral infection to over half the world's population. Modern jet travel and human emigration have facilitated global distribution of dengue serotypes, such that now multiple serotypes of dengue are endemic in many regions. Accompanying this, in the last 15 years has been an increase in the frequency of dengue epidemics and the incidence of dengue hemorrhagic fever and dengue shock syndrome. For example, in Southeast Asia, dengue hemorrhagic fever and dengue shock syndrome is a leading cause of hospitalization and death among children.

Effective vaccines exist for only a few members of the genus *Flavivirus*, including YF and JE, but there are no effective treatments for the diseases caused by any of the flaviviruses, including dengue, TBE and WN. Many of the viruses in this genus are particularly hazardous and present a serious health risk if released in the United States either by natural routes of infection or by a premeditated attack on the American populace.

In view of the above, a need remains for methods which inhibit the activity of flaviviruses and other viruses, either by inhibiting their propagation or otherwise. The present invention is directed, in part, to addressing this need.

SUMMARY OF THE INVENTION

The present invention relates to a polypeptide comprising an amino acid sequence corresponding to CCXXXCKEG-XXC (SEQ ID NO:1).

The present invention also relates to methods for inhibiting the activity of a virus. The method includes contacting the virus with a miniprotein ligand under conditions effective for the miniprotein ligand to bind to the virus.

The present invention, in another aspect thereof, relates to methods for detecting a virus in a sample. The method includes contacting the sample with a miniprotein ligand and determining whether the miniprotein ligand is bound to a virus.

The present invention also relates to a method of assessing a compound's usefulness in inhibiting the activity of a virus. The method includes contacting a virus with a compound to be screened in the presence of a miniprotein ligand which binds to the virus and determining whether the compound affects the binding of the miniprotein ligand to the virus.

BRIEF DESCRIPTION OF THE DRAWINGS

FIG. 1 is a graphic showing the amino acid sequence of conotoxin GI α and a polypeptide in accordance with the present invention as well as schematic representations of the two covalent forms of the polypeptide in accordance with the present invention.

FIG. 2 is a graph showing the results of a titration binding study of OHF-E-D3 with a polypeptide in accordance with the present invention.

DETAILED DESCRIPTION OF THE INVENTION

Figure 3:
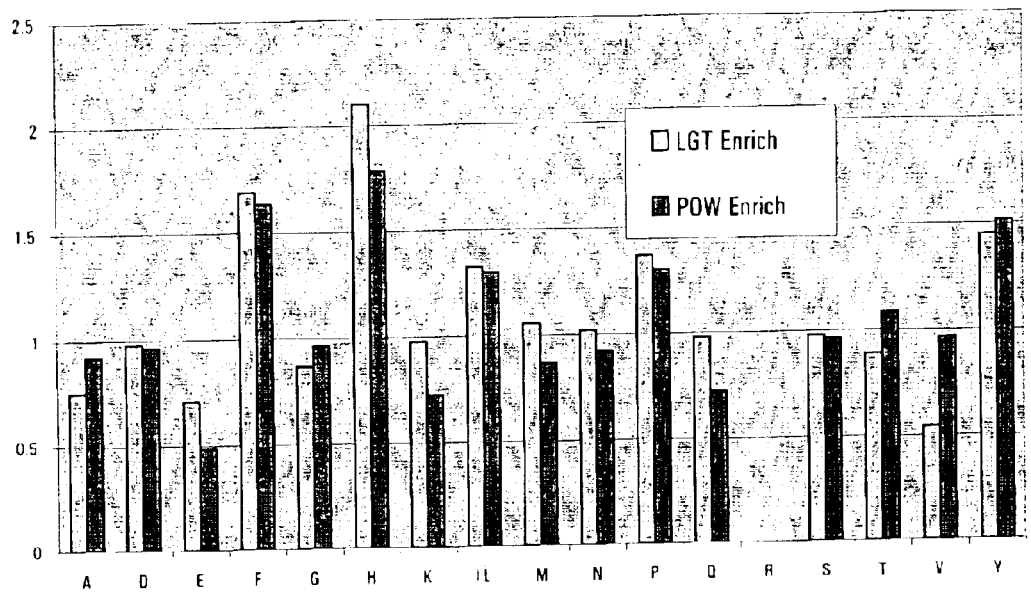
FIG. 3 is a bar graph showing the levels of LGT and POW enrichment, expressed as a ratio of enriched signal/library signal, for each amino acid in an MP-100N XPQ library.

One aspect of the present invention relates to a polypeptide which comprises an amino acid sequence corresponding to CCXXXXCKEGXXC (SEQ ID NO:1), such as a polypeptide which comprises an amino acid sequence of SEQ ID NO:1. Examples of such polypeptides include those which comprise an amino acid sequence corresponding to one of the following sequences:

| | |
|---|---|
| CCHPQCKEGXXC | SEQ ID NO:2 |
| CCGYACKEGXXC | SEQ ID NO:3 |
| CCVLACKEGXXC | SEQ ID NO:4 |
| CCATVCKEGXXC | SEQ ID NO:5 |
| CCELGCKEGXXC | SEQ ID NO:6 |
| CCTAVCKEGXXC | SEQ ID NO:7 |
| CCREPCKEGXXC | SEQ ID NO:8 |
| CCVSVCKEGXXC | SEQ ID NO:9 |
| CCTLRCKEGXXC | SEQ ID NO:10 |
| CCVRQCKEGXXC | SEQ ID NO:11 |
| CCTPTCKEGXXC | SEQ ID NO:12 |
| CCEYDCKEGXXC | SEQ ID NO:13 |
| | |
| CCXXXCKEGKXC | SEQ ID NO:14 |
| CCHPQCKEGKXC | SEQ ID NO:15 |
| CCGYACKEGKXC | SEQ ID NO:16 |
| CCVLACKEGKXC | SEQ ID NO:17 |
| CCATVCKEGKXC | SEQ ID NO:18 |
| CCELGCKEGKXC | SEQ ID NO:19 |
| CCTAVCKEGKXC | SEQ ID NO:20 |
| CCREPCKEGKXC | SEQ ID NO:21 |
| CCVSVCKEGKXC | SEQ ID NO:22 |
| CCTLRCKEGKXC | SEQ ID NO:23 |
| CCVRQCKEGKXC | SEQ ID NO:24 |
| CCTPTCKEGKXC | SEQ ID NO:25 |
| CCEYDCKEGKXC | SEQ ID NO:26 |
| | |
| CCXXXCKEGXKC | SEQ ID NO:27 |
| CCHPQCKEGXKC | SEQ ID NO:28 |
| CCGYACKEGXKC | SEQ ID NO:29 |
| CCVLACKEGXKC | SEQ ID NO:30 |
| CCATVCKEGXKC | SEQ ID NO:31 |
| CCELGCKEGXKC | SEQ ID NO:32 |
| CCTAVCKEGXKC | SEQ ID NO:33 |
| CCREPCKEGXKC | SEQ ID NO:34 |
| CCVSVCKEGXKC | SEQ ID NO:35 |
| CCTLRCKEGXKC | SEQ ID NO:36 |
| CCVRQCKEGXKC | SEQ ID NO:37 |
| CCTPTCKEGXKC | SEQ ID NO:38 |
| CCEYDCKEGXKC | SEQ ID NO:39 |
| | |
| CCXXXCKEGXNC | SEQ ID NO:40 |
| CCHPQCKEGXNC | SEQ ID NO:41 |
| CCGYACKEGXNC | SEQ ID NO:42 |
| CCVLACKEGXNC | SEQ ID NO:43 |
| CCATVCKEGXNC | SEQ ID NO:44 |
| CCELGCKEGXNC | SEQ ID NO:45 |
| CCTAVCKEGXNC | SEQ ID NO:46 |
| CCREPCKEGXNC | SEQ ID NO:47 |
| CCVSVCKEGXNC | SEQ ID NO:48 |
| CCTLRCKEGXNC | SEQ ID NO:49 |
| CCVRQCKEGXNC | SEQ ID NO:50 |
| CCTPTCKEGXNC | SEQ ID NO:51 |
| CCEYDCKEGXNC | SEQ ID NO:52 |
| | |
| CCXXXCKEGRXC | SEQ ID NO:53 |
| CCHPQCKEGRXC | SEQ ID NO:54 |
| CCGYACKEGRXC | SEQ ID NO:55 |
| CCVLACKEGRXC | SEQ ID NO:56 |
| CCATVCKEGRXC | SEQ ID NO:57 |
| CCELGCKEGRXC | SEQ ID NO:58 |
| CCTAVCKEGRXC | SEQ ID NO:59 |
| CCREPCKEGRXC | SEQ ID NO:60 |
| CCVSVCKEGRXC | SEQ ID NO:61 |
| CCTLRCKEGRXC | SEQ ID NO:62 |
| CCVRQCKEGRXC | SEQ ID NO:63 |
| CCTPTCKEGRXC | SEQ ID NO:64 |
| CCEYDCKEGRXC | SEQ ID NO:65 |
| | |
| CCXXXCKEGKKC | SEQ ID NO:66 |
| CCHPQCKEGKKC | SEQ ID NO:67 |
| CCGYACKEGKKC | SEQ ID NO:68 |
| CCVLACKEGKKC | SEQ ID NO:69 |
| CCATVCKEGKKC | SEQ ID NO:70 |
| CCELGCKEGKKC | SEQ ID NO:71 |
| CCTAVCKEGKKC | SEQ ID NO:72 |
| CCREPCKEGKKC | SEQ ID NO:73 |
| CCVSVCKEGKKC | SEQ ID NO:74 |
| CCTLRCKEGKKC | SEQ ID NO:75 |
| CCVRQCKEGKKC | SEQ ID NO:76 |
| CCTPTCKEGKKC | SEQ ID NO:77 |
| CCEYDCKEGKKC | SEQ ID NO:78 |
| | |
| CCXXXCKEGKNC | SEQ ID NO:79 |
| CCHPQCKEGKNC | SEQ ID NO:80 |
| CCGYACKEGKNC | SEQ ID NO:81 |
| CCVLACKEGKNC | SEQ ID NO:82 |
| CCATVCKEGKNC | SEQ ID NO:83 |
| CCELGCKEGKNC | SEQ ID NO:84 |
| CCTAVCKEGKNC | SEQ ID NO:85 |
| CCREPCKEGKNC | SEQ ID NO:86 |
| CCVSVCKEGKNC | SEQ ID NO:87 |
| CCTLRCKEGKNC | SEQ ID NO:88 |
| CCVRQCKEGKNC | SEQ ID NO:89 |
| CCTPTCKEGKNC | SEQ ID NO:90 |
| CCEYDCKEGKNC | SEQ ID NO:91 |
| | |
| CCXXXCKEGRKC | SEQ ID NO:92 |
| CCHPQCKEGRKC | SEQ ID NO:93 |
| CCGYACKEGRKC | SEQ ID NO:94 |
| CCVLACKEGRKC | SEQ ID NO:95 |
| CCATVCKEGRKC | SEQ ID NO:96 |
| CCELGCKEGRKC | SEQ ID NO:97 |
| CCTAVCKEGRKC | SEQ ID NO:98 |
| CCREPCKEGRKC | SEQ ID NO:99 |
| CCVSVCKEGRKC | SEQ ID NO:100 |
| CCTLRCKEGRKC | SEQ ID NO:101 |
| CCVRQCKEGRKC | SEQ ID NO:102 |
| CCTPTCKEGRKC | SEQ ID NO:103 |
| CCEYDCKEGRKC | SEQ ID NO:104 | as well as those which comprise an amino acid sequence of one of SEQ ID NO:2 through SEQ ID NO:104.

Another aspect of the present invention relates to a polypeptide which comprises an amino acid sequence corresponding to CCXXXCXEGKKC (SEQ ID NO:105), CCXXXCKXGKKC (SEQ ID NO:106), CCXXXCKEXKKC (SEQ ID NO:107), CCXXXCXEGKNC (SEQ ID NO:108), CCXXXCKXGKNC (SEQ ID NO:109), CCXXXCKEXKNC (SEQ ID NO:110), CCXXXCXEGRKC (SEQ ID NO:111), CCXXXCKXGRKC (SEQ ID NO:112), or CCXXXCKEXRKC (SEQ ID NO:113); as well as to a polypeptide which comprises an amino acid sequence of SEQ ID NO:105, SEQ ID NO:106, SEQ ID NO:107, SEQ ID NO:108, SEQ ID NO:109, SEQ ID NO:110, SEQ ID NO:111, SEQ ID NO:112, or SEQ ID NO:113. Examples of such polypeptides include those which comprise an amino acid sequence corresponding to one of the following sequences:

| | |
|---|---|
| CCHPQCKEGKKC | SEQ ID NO:114 |
| CCGYACKEGKNC | SEQ ID NO:115 |
| CCVLACKEGKKC | SEQ ID NO:116 |
| CCATVCKEGKKC | SEQ ID NO:117 |
| CCELGCKEGKKC | SEQ ID NO:118 |
| CCTAVCKEGKKC | SEQ ID NO:119 |
| CCREPCKEGRKC | SEQ ID NO:120 |
| CCVSVCKEGKKC | SEQ ID NO:121 |
| CCTLRCKEGKKC | SEQ ID NO:122 |
| CCVRQCKEGKKC | SEQ ID NO:123 |
| CCTPTCKEGKKC | SEQ ID NO:124 |
| CCEYDCKEGKKC | SEQ ID NO:125 |
| | |
| CCHPQCKXGKKC | SEQ ID NO:126 |
| CCGYACKXGKNC | SEQ ID NO:127 |
| CCVLACKXGKKC | SEQ ID NO:128 |
| CCATVCKXGKKC | SEQ ID NO:129 |

-continued

| | |
|---|---|
| CCELGCKXGKKC | SEQ ID NO:130 |
| CCTAVCKXGKKC | SEQ ID NO:131 |
| CCREPCKXGRKC | SEQ ID NO:132 |
| CCVSVCKXGKKC | SEQ ID NO:133 |
| CCTLRCKXGKKC | SEQ ID NO:134 |
| CCVRQCKXGKKC | SEQ ID NO:135 |
| CCTPTCKXGKKC | SEQ ID NO:136 |
| CCEYDCKXGKKC | SEQ ID NO:137 |
| | |
| CCHPQCKEXKKC | SEQ ID NO:138 |
| CCGYACKEXKNC | SEQ ID NO:139 |
| CCVLACKEXKKC | SEQ ID NO:140 |
| CCATVCKEXKKC | SEQ ID NO:141 |
| CCELGCKEXKKC | SEQ ID NO:142 |
| CCTAVCKEXKKC | SEQ ID NO:143 |
| CCREPCKEXRKC | SEQ ID NO:144 |
| CCVSVCKEXKKC | SEQ ID NO:145 |
| CCTLRCKEXKKC | SEQ ID NO:146 |
| CCVRQCKEXKKC | SEQ ID NO:147 |
| CCTPTCKEXKKC | SEQ ID NO:148 |
| CCEYDCKEXKKC | SEQ ID NO:149 | as well as those which comprise an amino acid sequence of one of SEQ ID NO:114 through SEQ ID NO:149. Other examples of such polypeptides include those which comprise an amino acid sequence corresponding to one of SEQ ID NO:105, SEQ ID NO:106, SEQ ID NO:107, SEQ ID NO:108, SEQ ID NO:109, SEQ ID NO:110, SEQ ID NO:111, SEQ ID NO:112, or SEQ ID NO:113 in which at least one of the three X's immediately to the right of the cysteine dimer (CC) is a glycine residue.

Unless otherwise specified, each of the amino acid residues marked X in each of SEQ ID NO:1 through SEQ ID NO:149 independently represents any amino acid residue other than cysteine.

Polypeptides of the present invention include those which contain, at a minimum, one of the aforementioned SEQ ID NO:1 through SEQ ID NO:149. The polypeptides of the present invention can also contain one or more other moieties that are bonded to the N-terminus, to the C-terminus, or to both the N-terminus and C-terminus of the aforementioned SEQ ID NO:1 through SEQ ID NO:149. Illustratively, the polypeptides of the present invention can include, in addition to one of the aforementioned SEQ ID NO:1 through SEQ ID NO:149, one or more additional amino acid residues bonded to the N-terminus, to the C-terminus, or to both the N-terminus and C-terminus of the aforementioned SEQ ID NO:1 through SEQ ID NO:149. For example, the polypeptide of the present invention can be a polypeptide which contains SEQ ID NO:1 and which is flanked by one additional amino acid residue at the C-terminus and by one additional amino acid residue at the N-terminus, as in the case where the polypeptide of the present invention is a polypeptide which contains one of SEQ ID NO:1 through SEQ ID NO:149 that is flanked, at each of the C-terminus and N-terminus, by a single amino acid residue selected from the group consisting of arginine, lysine, aspartic acid, and glutamic acid, for example, to improve the solubility of the polypeptide in aqueous media. Examples of such polypeptides include RCCXXXCKEGXXCR (SEQ ID NO:150), RCCXXXCKEGKXCR (SEQ ID NO:151), RCCXXXCKEGRXCR (SEQ ID NO:152), RCCXXXCKEGXNCR (SEQ ID NO:153), RCCXXXCKEGKKCR (SEQ ID NO:154), RCCXXXCKEGRKCR (SEQ ID NO:155), RCCXXXCKEGKNCR (SEQ ID NO:156), RCCHPQCKEGKKCR (SEQ ID NO:157), RCCGYACKEGKNCR (SEQ ID NO:158), RCCVLACKEGKKCR (SEQ ID NO:159), RCCATVCKEGKKCR (SEQ ID NO:160), RCCELGCKEGKKCR (SEQ ID NO:161), RCCTAVCKEGKKCR (SEQ ID NO:162), RCCREPCK-EGRKCR (SEQ ID NO:163), RCCVSVCKEGKKCR (SEQ ID NO:164), RCCTLRCKEGKKCR (SEQ ID NO:165), RCCVRQCKEGKKCR (SEQ ID NO:166), RCCTPTCKEGKKCR (SEQ ID NO:167), and RCCEYDCKEGKKCR (SEQ ID NO:168). Unless otherwise specified, each of the amino acid residues marked X in each of SEQ ID NO:150 through SEQ ID NO:168 independently represents any amino acid residue other than cysteine. As further illustration, the polypeptides of the present invention can include, in addition to one of the aforementioned SEQ ID NO:1 through SEQ ID NO:149, one or more (e.g., 1, 2, 3, 4, etc.) additional amino acid sequences selected from SEQ ID NO:1 through SEQ ID NO:149, which one or more additional amino acid sequences can be the same as or different. For example, where the polypeptide of the present invention includes two or more amino acid sequences selected independently from SEQ ID NO:1 through SEQ ID NO:149, these two or more amino acid sequences can be adjacent to one another, or they can be separated from one another by a linking group, such as a peptide or other organic moiety (e.g., an ethylene glycol moiety).

Suitable polypeptides include those which contain 12–1000 amino acids, such as 12–500 amino acids, 12–200 amino acids, 12–50 amino acids, 12–40 amino acids, 12–25 amino acids, 14–1000 amino acids, 14–500 amino acids, 14–200 amino acids, 14–50 amino acids, 14–40 amino acids, and/or 14–25 amino acids. Specific examples of such polypeptides include those which contain 12, 13, 14, 15, 16, 17, 18, 19, 20, 21, 22, 23, 24, 25, 26, 27, 28, 29, or 30 amino acids.

The polypeptides of the present invention can be isolated. The phrase "isolated", when referring to a polypeptide or other material, means a chemical composition which is not contained in an organism or an organism's cell in which it is naturally found. The isolated polypeptide or other material can be "purified", i.e., substantially free from other biological components. Preferably, the polypeptide is in a homogeneous state, which is meant to include homogeneous dry (e.g., lyophilized) polypeptides or homogeneous polypeptides in aqueous solution. Purity and homogeneity are typically determined using analytical chemistry techniques such as polyacrylamide gel electrophoresis or high performance liquid chromatography. A polypeptide which is the predominant species present in a preparation is, for the purposes of the present invention, to be considered substantially purified. Generally, a purified, isolated polypeptide will comprise more than 80% of all macromolecular species present in the preparation. Preferably, the polypeptide is purified such that it represents greater than 90% of all macromolecular species present. More preferably the polypeptide is purified to greater than 95%, and most preferably the polypeptide is purified to substantial homogeneity, wherein other macromolecular species are not detected by conventional techniques. "Purified" and "isolated" polypeptides can be synthetically or chemically produced, or they can be isolated from mixtures of materials produced by digestion of naturally occurring materials.

It will be readily understood by those skilled in the art and it is intended here, that when reference is made to particular sequence listings, such reference includes sequences which substantially correspond to those described including allowances for minor sequencing errors, single amino acid changes, deletions, substitutions, and the like. Further, it will be understood that the polypeptides of the present invention can contain naturally-occurring or non-naturally-occurring amino acids, including the D-form of the amino acids, amino acid derivatives, and amino acid mimics. Illustratively, "C", as used in the sequences set forth herein, are meant to include selenocysteine residues. Thus, for example, one or more (e.g., 1, 2, 3, or 4) of residues marked "C" in the sequences set forth herein can be replaced with a selenocysteine, for example, to reduce the likelihood of disulfide reduction either in the cytoplasm or when used in a detection format. The choice of including an (L)- or a (D)-amino acid in the polypeptides depends, in part, on the desired characteristics of the polypeptide. For example, the incorporation of one or more (D)-amino acids can confer increased stability on the polypeptide and can allow a polypeptide to remain active for an extended period of time. The polypeptides of the present invention may also be cyclized. As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine. In addition, modifications to the polypeptide backbone and polypeptide bonds thereof are also encompassed within the scope of amino acid mimic or mimetic. Such modifications can be made to the amino acid, derivative thereof, non-amino acid moiety or the polypeptide either before or after the amino acid, derivative thereof or non-amino acid moiety is incorporated into the polypeptide. What is critical is that such modifications mimic the polypeptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., *J. Org. Chem.*, 46:257 (1981) and Raucher et al., *Tetrahedron Lett.*, 21:14061 (1980), which are hereby incorporated by reference. An amino acid mimic is, therefore, an organic molecule that retains the similar amino acid pharmacophore groups as is present in the corresponding amino acid and which exhibits substantially the same spatial arrangement between functional groups. The substitution of amino acids by non-naturally occurring amino acids and amino acid mimics as described above can enhance the overall activity or properties of an individual polypeptide based on the modifications to the backbone or side chain functionalities. For example, these types of alterations to the amino acid substituents and polypeptides can enhance the polypeptide's stability to enzymatic breakdown. Modifications to the polypeptide backbone similarly can add stability and enhance activity.

More particularly, as used herein, "a polypeptide which comprises an amino acid sequence of" a specified sequence is meant to include only those polypeptides which include the exact specified sequence. As used herein, "a polypeptide comprising an amino acid sequence corresponding to" a specified sequence is meant to include those polypeptides which include the exact specified sequence as well as those polypeptides which include sequences having substantial identity with the specified sequence and those polypeptides which include sequences having substantial homology with the specified sequence.

The following terms are used to describe the sequence relationships between two or more amino acid sequences of polypeptides: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence.

As applied to polypeptides, the terms "substantial identity" or "substantial sequence identity" mean that two peptide sequences share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which have approximately the designated percentage of the same amino acids. For example, "95% amino acid identity" refers to a comparison of the amino acids of two polypeptides which have 95% amino acid identity. Preferably, residue positions which are not identical differ by conservative amino acid substitutions. For example, the substitution of amino acids having similar chemical properties such as charge, polarity, or hydrogen bonding characteristics are not likely to affect the properties of a polypeptide of the present invention. Examples include glutamine for asparagine, glutamic acid for aspartic acid, and glutamine for glutamic acid. Illustratively, the glutamic acid residue (E) in SEQ ID NO:1 and other such sequences can be replaced with a glutamine residue (Q).

As further applied to polypeptides, the terms "substantial homology" or "substantial sequence homology" mean that two peptide sequences share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which have approximately the designated percentage of the same amino acids or conservatively substituted amino acids. For example, "95% amino acid homology" refers to a comparison of the amino acids of two polypeptides which have 95% amino acid homology. As used herein, homology refers to identical amino acids or residue positions which are not identical but differ only by conservative amino acid substitutions. For example, the substitution of amino acids having similar chemical properties such as charge, polarity, or hydrogen bonding characteristics are not likely to affect the properties of a polypeptide of the present invention. Examples include glutamine for asparagine, glutamic acid for aspartic acid, and glutamine for glutamic acid. Illustratively, the glutamic acid residue (E) in SEQ ID NO:1 and other such sequences can be replaced with a glutamine residue (Q).

In view of the above discussion, it will be appreciated that "a polypeptide comprising an amino acid sequence corresponding to", for example, one of SEQ ID NO:1 through SEQ ID NO:104 is meant to include those polypeptides which include the exact specified sequence as well as those polypeptides in which the glutamic acid residue (E) that is positioned between and adjacent to the lysine residue and the glycine residue in the specified sequence (i.e., in one of SEQ ID NO:1 through SEQ ID NO:104) is replaced with a glutamine residue (Q). Illustratively, "a polypeptide comprising an amino acid sequence corresponding to" each of SEQ ID NO:1, SEQ ID NO:12, SEQ ID NO:25, SEQ ID NO:38, and SEQ ID NO:77 is meant to encompass a polypeptide which comprises an amino acid sequence of CCTPTCKQGKKC (SEQ ID NO:169) and, again, illustratively, "a polypeptide comprising an amino acid sequence corresponding to" SEQ ID NO:167 is meant to encompass a polypeptide which comprises an amino acid sequence of RCCTPTCKQGKKCR (SEQ ID NO:170).

The polypeptides of the present invention contain a plurality of cysteine residues, for example, denoted with "C" in SEQ ID NO:1 through SEQ ID NO:170. These cysteine residues can be present in any suitable form. For example, as discussed above, one or more of these residues can be present as the seleno analog of cysteine. Additionally or alternatively, the cysteine reside can be present in the reduced form, such as in the case where the cysteine residue is present as a free sulfhydryl (or free selenohydryl) or as a blocked sulfhydryl (or blocked selenohydryl), for example, with an acetamidomethyl ("ACM") group; or the cysteine reside can be present in the oxidized form, for example, as in the case where it is involved in a disulfide bond, in a diselenide bond, or in a S—Se bond.

As indicated above, polypeptides of the present invention can contain disulfide bonds between at least two of the cysteine residues. Illustratively, where the polypeptide contains 14 amino acids and comprises an amino acid sequence of RCCXXXCKEGXXCR (SEQ ID NO:150), the polypeptide can contain disulfide bonds between Cys2 and Cys13, between Cys3 and Cys7, between Cys2 and Cys7, and/or between Cys3 and Cys13). Polypeptides of the present invention which contain disulfide bonds between at least two of the cysteine residues can be made, for example, from polypeptides of the present invention which do not contain disulfide bonds, for example, by using conventional blocking group chemistry. Illustratively, disulfide bond formation can be controlled by using ACM blocking groups on two of the cysteine residues, permitting disulfide bonds formation to occur (e.g., via air oxidation) between the unblocked cysteines, removing the ACM blocking groups (e.g., by exposure to iodine), and permitting disulfide bonds formation to occur (e.g., via air oxidation) between the deblocked cysteines.

One skilled in the art, using the above sequences or formulae, can readily synthesize the polypeptides of the present invention. Standard procedures for preparing synthetic polypeptides are well known in the art. For example, the novel polypeptides can be synthesized using: the solid phase peptide synthesis ("SPPS") method of Merrifield (*J. Am. Chem. Soc.,* 85:2149–2154 (1964), which is hereby incorporated by reference) or modifications of SPPS; or the peptides can be synthesized using standard solution methods well known in the art (see, for example, Bodanzsky, *Principles of Peptide Synthesis,* 2nd revised ed., Berlin-N.Y.: Springer-Verlag (1988 and 1993), which is hereby incorporated by reference). Alternatively, simultaneous multiple peptide synthesis ("SMPS") techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described in Houghten, *Proc. Natl. Acad. Sci., USA,* 82:5131–5135 (1985), which is hereby incorporated by reference.

Alternatively, the polypeptides of the present invention can be produced recombinantly. Accordingly the present invention also relates to nucleic acid molecules (e.g., DNA or RNA molecules) encoding the polypeptides of the present invention, as well as to expression vectors, expression systems, cells, organisms, and/or the like containing such nucleic acid molecules. Such nucleic acid molecules (e.g., DNA or RNA molecules) encoding the polypeptides of the present invention, as well as such expression vectors, expression systems, cells, organisms, etc. containing such nucleic acid molecules can be used to recombinantly produce the polypeptides of the present invention.

Nucleic acid molecules of the present invention can also be used to assemble a library of nucleic acid molecules encoding one or more of the polypeptides of the present invention. By panning such a library of nucleic acid molecules against a target protein (e.g., a virus protein or any other protein or portion thereof, such as Domain III of a flavivirus envelope protein), one can identify polypeptides which bind especially well to the target protein, for example, in order to optimize selection of one of the polypeptides of the present invention against a particular target protein or against a particular group of target proteins. Accordingly, in addition to being directed to nucleic acid molecules encoding polypeptides of the present invention, the present invention is also directed to libraries or other types of assemblages of such nucleic acid molecules which include two or more nucleic acid molecules encoding two or more different polypeptides of the present invention. The nucleic acids of the present invention can be isolated, purified, both isolated and purified, or neither isolated nor purified.

The present invention further relates to an antibody or fragment thereof specific for one or more of the polypeptides of the present invention. Antibodies of the subject invention include polyclonal antibodies and monoclonal antibodies capable of binding to the polypeptides of the present invention, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the $F(ab')_2$, and the Fc fragments. Suitable antibodies or fragments thereof include those which are specific for a polypeptide of the present invention.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (e.g., see Campbell, *Monoclonal Antibody Technology: Laboratory Techniques in Biochemistry and Molecular Biology,* Amsterdam, The Netherlands: Elsevier Science Publishers (1984) and St. Groth et al., *J. Immunol. Methods,* 35:1–21 (1980) ("Campbell"), which are hereby incorporated by reference). Any animal (mouse, rabbit, etc.) which is known to produce antibodies can be immunized with the antigenic polypeptides of the present invention (or an antigenic fragment thereof). Methods for immunization are well known in the art. Such methods include subcutaneous or intraperitoneal injection of the polypeptide. One skilled in the art will recognize that the amount of the polypeptide used for immunization will vary based on the animal which is immunized, the antigenicity of the polypeptide, and the site of injection.

The polypeptide which is used as an immunogen may be modified or administered in an adjuvant in order to increase the polypeptide's antigenicity. Methods of increasing the antigenicity of a polypeptide are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O—Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell. Res.*, 175:109–124 (1988), which is hereby incorporated by reference).

Hybridomas secreting the desired antibodies are cloned and the class and subclass are determined using procedures known in the art (see, e.g., Campbell, which is hereby incorporated by reference).

For polyclonal antibodies, antibody containing antisera is isolated from the immunized animal and is screened for the presence of antibodies with the desired specificity using one of the above-described procedures.

In accordance with the above discussion, the subject invention further provides a method of producing an antibody specific for a polypeptide of the present invention in a host. The method comprises selecting the isolated polypeptide of the present invention or an antigenic portion thereof and introducing the selected polypeptide of the present invention or antigenic portion thereof into a host to induce production of an antibody specific for polypeptide of the present invention in the host.

The present invention also relates to the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art (for example, see Sternberger et al., *J. Histochem. Cytochem.*, 18:315–333 (1970); Bayer et al., *Meth. Enzym.*, 62:308–315 (1979); Engvall et al., *J. Immunol.*, 109:129–135 (1972); and Goding, *J. Immunol. Meth.*, 13:215–226 (1976), each of which is hereby incorporated by reference).

The labeled antibodies or fragments thereof of the present invention can be used for in vitro, in vivo, and in situ assays to determine the presence or absence of a polypeptide of the present invention in a sample. For example, the antibodies or fragments thereof of the present invention can be used in conjunction with a polypeptide of the present invention to detect flaviviruses in biological or non-biological samples. Illustratively, a sample which may or may not contain a flavivirus is contacted with a polypeptide of the present invention under conditions effective for the polypeptide to bind to the flavivirus (if the flavivirus is present in the sample); unbound polypeptide is then rinsed off or otherwise removed; and the sample is then contacted with a labeled antibody (or fragment thereof) of the present invention under conditions effective for the antibody to bind to any polypeptide which may be present in the sample. Unbound antibody is then removed (e.g., by washing), and the presence of antibody is detected (e.g., by fluorescence in the case of a fluorescently labeled antibody). The presence of antibody indicates the presence of polypeptide which, in turn, indicates the presence of flavivirus in the sample. Antibodies or fragments thereof of the present invention can also be used for in vitro, in vivo, and in situ assays to determine the presence or absence of a polypeptide of the present invention in a sample for other purposes, such as to identify the mechanism by which the polypeptides of the present invention inhibit flavivirus propagation.

The present invention also relates to polypeptides of the present invention in labeled form. Such labeled polypeptides of the present invention can be used, for example, to detect flaviviruses in biological or non-biological samples. Suitable labels and methods for labeling the polypeptides of the present invention include those described above with regard to the labeling of antibodies.

The present invention, in another aspect thereof, relates to methods for inhibiting the activity of a flavivirus or other virus. The mechanism by which the method of the present invention inhibits the virus's activity is not particularly critical. Illustratively, in the case where the virus is a flavivirus, the activity of a flaviviruses can be inhibited by inhibiting the ability of the flavivirus to propagate (which is meant to include replication steps which take place outside a host cell as well as steps which take place inside a host cell); by inhibiting the ability of the flavivirus to bind to a target cell; by inhibiting the ability of the flavivirus to infect a target cell; by inhibiting the ability of the flavivirus to thrive in a transmission vector, by the miniprotein ligand's blocking of a binding site on the flavivirus's envelope protein; by the miniprotein ligand's inducing a conformational change in the flavivirus's envelope protein which conformational change renders the flavivirus less likely to bind to a target cell; by the miniprotein ligand's blocking of the physical or biological activity of a flavivirus envelope protein or other protein inside a host cell; or by any combination of these or other mechanisms.

In accordance with the method of the present invention, the activity of a flavivirus or other virus is inhibited by contacting the flavivirus or other virus with a miniprotein ligand, such a miniprotein ligand which is specific for an envelope protein of one or more flaviviruses, such as a miniprotein ligand which is specific for an envelope protein of one or more flaviviruses, examples of which include JE, WN, dengue virus (including the four serotypes of: dengue-1, dengue-2, dengue-3, and dengue-4), YF, TBE, central European TBE, OHF, KFD, Alkhurma viruses, RSSE, Kumlinge TBE, St. Louis encephalitis, Langat viruses, Powassan viruses, etc. For the purposes of the present invention, a miniprotein ligand is to be deemed to be "specific" for an envelope protein of a flavivirus if the miniprotein ligand binds to the flavivirus with a binding constant that is greater than 2 times (e.g., greater than 3 times, greater than 5 times, greater than 10 times) that of the binding constant between the miniprotein ligand and albumin.

As used herein, "miniprotein ligand" is meant to refer to a small (e.g., 10–50 residue), conformationally restrained polypeptides that adopt a persistent structure. Illustratively, "miniprotein ligand" is meant to include small (e.g., 10–50 residue), disulfide rich (e.g., containing two or more disulfide bonds or containing amino acid residues capable of forming two or more disulfide bonds), conformationally restrained polypeptides that adopt a persistent structure, for example, polypeptides which comprise 4 or more cysteine residues that are arranged to allow formation of multiple disulfide bonds. As further illustration, "miniprotein ligand" is meant to include, for example, polypeptides which have the cysteine scaffold of conotoxin GI (e.g., polypeptides which comprise an amino acid sequence corresponding to CCXXXCXXXXXC (SEQ ID NO:171), such as RCCXXX-CXXXXXCR (SEQ ID NO:172), as well as those which comprise an amino acid sequence of SEQ ID NO:171, such as SEQ ID NO:172). Examples of such miniprotein ligands which can be used in the method of the present invention include polypeptides which comprise an amino acid sequence corresponding to one or more of SEQ ID NO:1 through SEQ ID NO:170; as well as polypeptides which comprise an amino acid sequence of one or more of SEQ ID NO:1 through SEQ ID NO:170.

Alternatively, the "miniprotein ligand" can be a polypeptide which has the cysteine scaffold of a cysteine-rich toxin other than conotoxin GI, such as conotoxins other than conotoxin GI. Additionally or alternatively, the "miniprotein ligand" can be a polypeptide which has 10–50 amino acid residues; of which at least 4 are cysteine residues; provided that, of the 4 cysteine residues, 3 are not adjacent to one another.

Still additionally or alternatively, the "miniprotein ligand" can be a polypeptide which has 10–50 amino acid residues; of which at least 4 are cysteine residues; provided that, of the 4 cysteine residues, 3 are not adjacent to one another; and further provided that, of the 4 cysteine residues, 2 are adjacent to one another. Still additionally or alternatively, the "miniprotein ligand" can be a polypeptide which has 10–50 amino acid residues; of which at least 4 are cysteine residues; provided that, of the 4 cysteine residues, 2 are adjacent to one another; and further provided that neither of the remaining two cysteine residues is adjacent to any of the other cysteine residues. Still additionally or alternatively, the "miniprotein ligand" can be a polypeptide which has 10–50 amino acid residues; of which at least 4 are cysteine residues; provided that, of the 4 cysteine residues, 2 are adjacent to one another; and further provided that each of the remaining two cysteine residues is separated from each of the other cysteine residues by at least 2 (e.g., by 2, by 3, by 4, by 5, by 6, by 7, and/or by 8) non-cysteine amino acid residues. Still additionally or alternatively, the miniprotein ligands can be polypeptides which comprise an amino acid sequence corresponding to RCCXXXCXXXXCR (SEQ ID NO:173); polypeptides which comprise an amino acid sequence of SEQ ID NO:173; polypeptides which comprise an amino acid sequence corresponding to RCCXXXCXXXXXCR (SEQ ID NO:174); polypeptides which comprise an amino acid sequence of SEQ ID NO:174; polypeptides which comprise an amino acid sequence corresponding to RCCXXXXCXXXXCR (SEQ ID NO:175); polypeptides which comprise an amino acid sequence of SEQ ID NO:175; polypeptides which comprise an amino acid sequence corresponding to RCCXXXXCXXXXXCR (SEQ ID NO:176); polypeptides which comprise an amino acid sequence of SEQ ID NO:176; polypeptides which comprise an amino acid sequence corresponding to RCCXXXXXCXXXXXCR (SEQ ID NO:177); polypeptides which comprise an amino acid sequence of SEQ ID NO:177.

Still additionally or alternatively, the "miniprotein-ligand" can be a polypeptide which has 10–50 amino acid residues; of which at least 4 are cysteine residues; provided that none of the 4 cysteine residues are adjacent to any of the other 3 cysteine residues. Still additionally or alternatively, the "miniprotein ligand" can be a polypeptide which has 10–50 amino acid residues; of which at least 4 are cysteine residues; provided that none of the 4 cysteine residues are adjacent to any other cysteine residue. Still additionally or alternatively, the "miniprotein ligand" can be a polypeptide which has 10–50 amino acid residues; of which at least 4 are cysteine residues; provided each of the 4 cysteine residues is separated from each of the other 4 cysteine residues by at least 1 (e.g., by 1, by 2, by 3, by 4, by 5, by 6, by 7 and/or by 8) non-cysteine amino acid residues.

As used herein, "miniprotein ligand" is meant to include two or more (e.g., 2, 3, 4, 5, etc.) miniprotein ligands which are adjacent to one another or which are separated from one another by a linking group, such as a peptide or other organic moiety (e.g., an ethylene glycol moiety).

As indicated above, the method of the present invention involves contacting the flavivirus or other virus with a miniprotein ligand. In this regard, it should be noted that "contacting the flavivirus or other virus with a miniprotein ligand" is meant to include situations where the miniprotein ligand is brought into contact with (i) an intact flavivirus or other virus particle; (ii) any portion of the flavivirus or other virus particle (e.g., the envelope protein, a portion of the envelope protein, any nucleic acid molecule which is part of the virus's genome, etc.); and/or (iii) a protein or other polypeptide that is encoded by the genome of the virus (e.g., a protein or other polypeptide which is encoded by the genome of the virus but which is expressed in a host cell).

Such contact can be carried out in vitro, for example, by spraying an area in which flavivirus is known or suspected to exist with the miniprotein ligand or with a composition containing a miniprotein ligand. Suitable compositions can include materials that are typically used in pesticide or herbicide applications, such as those containing inert oils, inert powders, dispersing agents, granulating agents, and the like. The compositions can also (i.e., in addition to the miniprotein ligand) include pesticides, pheromones, or other ingredients which are used to kill or otherwise control populations of one or more transmission vectors (e.g., ticks, mosquitos, etc.).

Such contact can also take place, in vivo, in an animal (e.g., insect, tick, birds, mammal, cat, dog, deer, pig, cow, horse, goat, human) harboring (e.g., being a transmission vector) or infected with a flavivirus. Where in vivo contact is desired, such contact can be carried out by administering an effective amount of the miniprotein ligand of the present invention to the animal.

Additionally or alternatively, the miniprotein ligand can be administered to animals (e.g., insect, tick, birds, mammal, cat, dog, deer, pig, cow, horse, goat, human) which are susceptible to harboring (e.g., susceptible to becoming a transmission vector) or susceptible to becoming infected with a flavivirus, so that, if such animal comes into contact with a flavivirus, propagation of the flavivirus will be inhibited or infection by the flavivirus will be inhibited, or the activity of the flavivirus will be otherwise inhibited.

Irrespective of whether the miniprotein ligand is administered for therapeutic or preventative purposes, it will be appreciated that the actual preferred effective amount of miniprotein ligand will vary according to the miniprotein ligand employed, the particular composition formulated, and the mode of administration. Many factors that can modify the miniprotein ligand's activity will be taken into account by those skilled in the art; e.g., species, body weight, sex, diet, time of administration, route of administration, rate of excretion, condition of the animal, and reaction sensitivities and severities.

Illustratively, the miniprotein ligand can be administered in a single daily dose or in multiple doses or even continuously. Continuous administration can be carried out in the inpatient setting (typically for humans or domestic mammals) by, for example, intravenous drip, or in an outpatient setting by providing the peptide in the form of pills, capsules, liquid suspensions, and/or slow-release formulations. The miniprotein ligand can be administered by any of the conventional modes of drug administration, including oral or parenteral administration. Examples of parenteral administration are intradermal, intraventricular, intracerebral, intramuscular, intravenous, intraperitoneal, rectal, and subcutaneous administration.

The miniprotein ligand of the present invention can be administered alone or in combination with suitable pharmaceutical carriers or diluents. The diluent or carrier ingredients should be selected so that they do not diminish the therapeutic or preventative effects of the miniprotein ligand.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology*, 3rd edition, Volume 15, New York: John Wiley and Sons, pp. 470–493 (1981), which is hereby incorporated by reference.

Miniprotein ligands which are useful in the practice of the method of the present invention can be prepared using conventional peptide chemistry, such as described above, or they can be produced recombinantly, for example, also as discussed above.

The present invention, in another aspect thereof, relates to methods for detecting a flavivirus or other virus in a sample. The method includes contacting the sample with a miniprotein ligand and determining whether the miniprotein ligand is bound to a flavivirus.

Suitable miniprotein ligands which can be used in this method of the present invention include those described hereinabove. Illustratively, TBE, YF, Dengue fever, Langat, Powassan, OHF, and WN viruses can be detected using a miniprotein ligand which comprises an amino acid sequence corresponding to one or more of SEQ ID NO:1 through SEQ ID NO:177; or by using a miniprotein ligand which comprises an amino acid sequence of one or more of SEQ ID NO:1 through SEQ ID NO:177.

In the practice of the method of the present invention, contacting can be carried out in vivo or in vitro.

Where contacting is carried out in vitro, the sample can be serum, a tissue sample, saliva, etc. taken from an animal who is suspected of being infected or a transmission vector for the flavivirus. The method of the present invention can also be used in the in vitro context to test for the presence of flavivirus on inanimate objects, such as air, envelopes, doorknobs, desk surfaces, kitchen utensils, and the like, either by contacting the inanimate object directly with the miniprotein ligand or by contacting the inanimate object with a transfer material (e.g., by wiping the inanimate object with a cotton-tipped swab or a cloth) and then contacting the transfer material with the miniprotein ligand.

Contacting can also be carried out in vivo to detect for the presence of a flavivirus in an animal (e.g., human, mosquito, tick, dog, cat, etc.) or other living sample. Where the method is carried out in vivo, the method of the present invention can be used to detect not only whether a flavivirus is present in the organism but also to determine the distribution of the flavivirus in the organism.

Irrespective of whether contact is made in vivo or in vitro, contacting should be carried out under conditions effective to permit the miniprotein ligand to bind to the flavivirus (if, indeed, flavivirus is present). Thus, for example, as one skilled in the art will appreciate, the contacting step should be carried out at temperatures, at concentrations, at ionic strengths, at for periods of time, etc. which do not inhibit or otherwise thwart the miniprotein ligand/flavivirus interaction (e.g., by denaturing one or both, by not allowing the two to interact for periods sufficient to permit binding, etc.). Typically, the contacting is carried out at about room temperature, at physiologically acceptable pH and ionic strengths, and for a conventional period of time (e.g., from about 15 minutes to about 4 hours). In this regard, it should be noted that the binding of a miniprotein ligand to a virus is meant to include situations where the miniprotein ligand binds to (i) an intact virus particle; (ii) any portion of the virus particle (e.g., an envelope protein, a portion of the envelope protein, any nucleic acid molecule which is part of the virus's genome, etc.); and/or (iii) a protein or other polypeptide that is encoded by the genome of the virus (e.g., a protein or other polypeptide which is encoded by the genome of the virus but which is expressed in a host cell).

Once the sample is contacted with the miniprotein ligand, the method of the present invention calls for determining whether the miniprotein ligand is bound to a flavivirus or other virus. "Bound", as used in this context, refers to any interaction, irrespective of whether such interaction is based on covalent interactions, hydrogen interactions, van der Waals interactions, physical interactions, ionic interactions, or combinations of these or other interactions. Furthermore, as discussed above, a miniprotein ligand is to be deemed as being bound to a flavivirus or other virus if the miniprotein ligand is bound to (i) an intact virus particle; (ii) any portion of the virus particle (e.g., an envelope protein, a portion of the envelope protein, any nucleic acid molecule which is part of the virus's genome, etc.); and/or (iii) a protein or other polypeptide that is encoded by the genome of the virus (e.g., a protein or other polypeptide which is encoded by the genome of the virus but which is expressed in a host cell). Typically, determining whether the miniprotein ligand is bound to a flavivirus or other virus involves removing (e.g., by washing, eluting, etc.) unbound miniprotein ligand from the sample and detecting any miniprotein ligand that remains in the sample (i.e., any miniprotein ligand that is bound to flavivirus). Detecting the miniprotein ligand can be carried out in any suitable fashion, such as by detecting the presence of a fluorescent, radioactive, or other label (in the case where a labeled miniprotein ligand was employed), by cleaving the miniprotein ligand from the flavivirus and using antibodies to detect the miniprotein ligand, or the like. It will be appreciated that, in some circumstances, it is important to know, not only whether flavivirus is present in a sample, but also the amount of flavivirus present in the sample. The detection method described above can readily be adapted to make such a determination and, the detection methods of the present invention are meant to encompass such quantitative determinations.

The present invention, in another aspect thereof, relates to a method for screening for or otherwise assessing a compound's usefulness in inhibiting the activity of a flavivirus or other virus. The method includes contacting a flavivirus or other virus with the compound to be screened in the presence of a miniprotein ligand which binds to the flavivirus or other virus and determining whether the compound affects the binding of the miniprotein ligand to the flavivirus or other virus. Illustratively, the compound that is to be screened can be screened alone or it can be screened as part of a collection (e.g., a library) of such compounds. Illustratively, the compound to be screened can be a compound which is not a polypeptide, a compound which does not contain any peptide bonds, a compound which has a molecular weight of less than 2000 g/mole, a compound which has a molecular weight of less that 1000 g/mole, and/or a compound which has a molecular weight of less than 500 g/mole. The method can be practiced by first binding the miniprotein ligand to the flavivirus (or other virus), then contacting this miniprotein ligand/flavivirus with the compound to be screened and determining whether and/or to what extent the compound being screened displaces the miniprotein ligand from the flavivirus. Alternatively, the method can be practiced by first permitting the compound to be screened to bind to the flavivirus (or other virus), then contacting this compound/flavivirus composition with the miniprotein ligand and determining whether and/or to what extent the miniprotein ligand displaces the compound from the flavivirus (to the extent that the compound binds to the flavivirus at all). Still alternatively, the compound to be screened and miniprotein ligand can be added to the flavivirus or other virus at the same time in a binding competition assay to determine which binds better and to what extent.

Suitable miniprotein ligands which can be used in this screening method of the present invention include those described hereinabove. Illustratively, where the flavivirus is TBE, YF, Dengue fever, Langat, Powassan, OHF, or WN virus, the screening method of the present invention can employ a miniprotein ligand which comprises an amino acid sequence corresponding to one or more of SEQ ID NO:1 through SEQ ID NO:177; or a miniprotein ligand which comprises an amino acid sequence of one or more of SEQ ID NO:1 through SEQ ID NO:177.

Irrespective of whether the flavivirus or other virus is contacted first with the miniprotein ligand, is contacted first with the compound to be screened, or is contacted simultaneously with the miniprotein ligand and the compound to be screened, all contacting should be carried out under conditions effective to permit the miniprotein ligand and compound to bind to the flavivirus or other virus. Thus, for example, as one skilled in the art will appreciate, all contacting should be carried out at temperatures, at concentrations, at ionic strengths, at for periods of time, etc. which do not inhibit or otherwise thwart the miniprotein ligand/virus interaction or the compound/virus interaction (e.g., by denaturing one or both, by not allowing the two to interact for periods sufficient to permit binding, etc.). Generally, the contacting is carried out at about room temperature, at physiologically acceptable pH and ionic strengths, and for period of time (e.g., from about 15 minutes to about 4 hours) which is typical for binding competition assays.

Once the virus is contacted with the miniprotein ligand and compound to be screened, the method of the present invention calls for determining whether the compound affects the binding of the miniprotein ligand to the flavivirus or other virus. For example, determining whether the compound affects the binding of the miniprotein ligand to the flavivirus or other virus can be carried out by determining whether and/or to what extent unbound miniprotein ligand is present in the sample. Detecting unbound miniprotein ligand can be carried out in any suitable fashion, such as by detecting the presence of a fluorescent, radioactive, or other label in eluent (in the case where a labeled miniprotein ligand is employed and the unbound miniprotein ligand is eluted), by detecting the presence of unbound miniprotein ligand using antibodies to the miniprotein ligand, and the like. Alternatively or additionally, determining whether the compound affects the binding of the miniprotein ligand to the flavivirus or other virus can be carried out by detecting unbound compound, by detecting the amount of miniprotein ligand/virus present in the reaction mixture (e.g. by NMR), and/or by detecting the amount of compound/virus present in the reaction mixture (e.g. by NMR).

As indicated above, the method of the present invention involves contacting the flavivirus or other virus with a miniprotein ligand and with a compound to be screened. In this regard, it should be noted that "contacting the flavivirus or other virus with a miniprotein ligand" and "contacting the flavivirus or other virus with a compound to be screened" is meant to include situations where the miniprotein ligand and compound are brought into contact with (i) an intact flavivirus or other virus particle; (ii) any portion of the flavivirus or other virus particle (e.g., the envelope protein, a portion of the envelope protein, any nucleic acid molecule which is part of the virus's genome, etc.); and/or (iii) a protein or other polypeptide that is encoded by the genome of the virus (e.g., a protein or other polypeptide which is encoded by the genome of the virus but which is expressed in a host cell). Moreover, the method of the present invention calls for "determining whether the compound affects the binding of the miniprotein ligand to the flavivirus or other virus. As one skilled in the art will appreciate, "binding", as used in this context, refers not only to binding of the miniprotein ligand to an intact flavivirus or other virus particle, but also to any portion of the flavivirus or other virus particle (e.g., the envelope protein, Domain III or some other portion of the envelope protein, any nucleic acid molecule which is part of the virus's genome, etc.) as well as to a protein or other polypeptide that is encoded by the genome of the virus (e.g., a protein or other polypeptide which is encoded by the genome of the virus but which is expressed in a host cell). Thus, by way of illustration, the method of the present invention can be carried out using a portion of a flavivirus envelope protein (e.g., Domain III of a flavivirus envelope protein), for example, by contacting Domain III of a flavivirus envelope protein with the compound to be screened in the presence of a miniprotein ligand which binds to Domain III of the flavivirus envelope protein and determining whether the compound affects the binding of the miniprotein ligand to Domain III of the flavivirus envelope protein.

Certain aspects of the present invention are further illustrated with the following examples.

EXAMPLES

Example 1

Cloning and Expression of Langat Envelope Protein Domain III

Langat Envelope Protein Domain III (LGT-E-D3) was generated as a GST fusion protein in *E. coli* using the pGEX-2T expression system (Pharmacia) and highly purified as previously described in Bhardwaj et al., "Biophysical Characterization and Vector-Specific Antagonist Activity of Domain III of the Tick-Borne Flavivirus Envelope Protein," *Journal of Virology,* 75(8):4002–4007 (2001), which is hereby incorporated by reference. The purified LGT-E-D3 was determined by circular dichroism analysis to have a structure similar to that of the crystal structure of the D3 component of a large soluble fragment of the central European TBE envelope protein as set forth in Rey et al., "The Envelope Glycoprotein from Tick-Borne Encephalitis at 2 Å Resolution," *Nature,* 375:291–298 (1995), which is hereby incorporated by reference. LGT-E-D3 was also found to be highly stable in up to 4 M urea. LGT-E-D3 has recently been cloned into a maltose-binding protein (MBP) expression system (New England Biolabs) that has resulted in an increased yield of D3 protein along with an increased ease of purification. In addition, the D3 from several flaviviruses have been cloned into the MBP system with protein expression yields similar to that of LGT-E-D3. These include D3 from DEN-4, WN, and YF viruses, and the tick-borne POW, OHF, KUM, and KFD viruses.

Example 2

Development of LGT-E-D3 Mutants

Several mutations in the LGT-E-D3 have been generated to examine residues that may be important to three D3 interactions: (a) D3 attachment to host cell, (2) miniprotein MP-100 binding, and (3) pentamer formation at acidic pH. These mutations were produced using a commercially available kit (QUICKCHANGE™ Mutagenesis kit, Stratagene) and are summarized in Table 1.

TABLE 1

| Residue | Mutation |
| --- | --- |
| E-309 | K - > del |
| E-320 | D - > A |
| E-324 | D - > A |
| E-324 | D - > G |
| E-377 | P - > G |
| E-378 | ins - > F |
| E-380 | D - > A |
| E-384 | Y - > V |
| E-394 | Q - > K |

As discussed below, LGT-E-D3 has been shown to bind to Vero cells, and most of the mutations created in LGT-E-D3 are charge group substitutions of surface exposed residues and insertions/deletions based on differences between mosquito-and tick-borne viruses. These mutants can be used to optimize the selection of particular miniprotein ligands by assisting in the determination of whether any of these residues are important to LGT-E-D3 binding to host cells.

Example 3

LGT-E-D3 Binds to Host Cells

The binding of D3 binding to host cells was investigated. Equilibrium-binding studies were performed on live Vero cells. This technique utilized iodinated ($^{125}$I-labelled) LGT-E-D3 binding to live Vero cells to demonstrate that LGT-E-D3 bound to Vero cells with single-site binding characteristics and an apparent $K_d$ of 25 µM. The data identify LGT-E-D3 as the appropriate target for miniprotein ligand development and optimization to inhibit cell attachment and entry. Further, the binding experiment serves as the basis for a competition experiment to test whether MP-100 or other miniprotein ligands block virus entry by competing with the receptor for LGT-E-D3 binding.

Example 4

Generation of a Miniprotein That Binds to LGT-E-D3

The α-conotoxin GI scaffold was selected to restrain the conformation of a five-residue peptide. The HPQ sequence was selected to replace NPA so as to favor a type I β-turn and to remove residues that might contribute to peptide toxicity. A phage display library was constructed using the FUSE5 M13-based vector that encoded gene3 fusions of the peptide RCCHPQCXXXXXCR (SEQ ID NO:178). The X residues represent any naturally occurring amino acid. A library of $5 \times 10^7$ members was created encoding >95% of the $3.2 \times 10^6$ possible peptide sequences. LGT-E-D3 was biotinylated (1–2 sites/protein) and bound to streptavidin beads that had been preincubated with iminobiotin to block 90% of sites, in an effort to reduce avidity effects. LGT-E-D3-biotin was added and the beads were blocked with biotin. Five rounds of panning converged to the sequence termed MP-100: RCCHPQCKEGKKCR (SEQ ID NO:157). The MP-100 peptide was synthesized with Tert- and Acm-Cys blocking groups that allowed the specific synthesis of nested (Cys2-Cys13, Cys3-Cys7) or crossed (Cys2-Cys7, Cys3-Cys13) disulfide bonds. These were termed MP-100N (N=nested) and MP-100C (C=crossed), respectively, and the two forms are shown in FIG. 1, along with the sequence for conotoxin GI α. The third possible disulfide pairing is strongly disfavored by a Cys2-Cys3 bond.

The affinity of both MP-100 peptides (MP-100N and MP-100C) to LGT-E-D3 was determined using fluorescence anisotropy spectroscopy. The LGT-E-D3 was fluoreceinated (1–2 labels per protein) and a 1 nM solution was titrated with each MP-100 peptide in 20 mM Hepes buffer, pH 7.4. The resulting binding behavior is complex, and the curve can be fit with two binding affinities, the constants for which are set forth in Table 2.

TABLE 2

| Virus-E-D3 | MP-100N $K_{d1}$ (µM) | MP-100N $K_{d2}$ (µM) | MP-100C $K_{d1}$ (µM) | MP-100C $K_{d2}$ (µM) |
| --- | --- | --- | --- | --- |
| LGT-E-D3 | 164 | 3050 | 60 | 2000 |
| OHF-E-D3 | 16 | 900 | 30 | 1800 |

The E-D3 molecules were pure and were run as monomers of sizing columns. The MP-100N and MP-100C peptides were pure and free of cross-contamination. We believe that both MP-100C and MP-100N bind to monomeric LGT-E-D3 with approximate apparent $K_d$ values of 60 and 164 µM respectively. We hypothesize that the weaker apparent affinity values (in the mM range) represents a thermodynamic linkage of MP-100 binding (across two adjacent monomers in an oligomer) to the oligomerization equilibrium of the oligomer. We have also investigated the binding of MP-100-to LGT-E-D3 in PBS. The result is a sigmoid curve that reaches much higher anisotropy values. The cooperative nature of MP-100 and phosphate binding suggests that MP-100 may stabilize an oligomer rather than having a second weak binding site. Studies are in progress to examine titrations of MP-100C and MP-100N to varying concentrations of LGT-E-D3 in Hepes buffer to test this hypothesis.

The experiment was repeated to study the binding of the MP-100C and MP-100N miniproteins to OHF-E-D3. As shown in Table 2, the MP-100C and MP-100N miniproteins bind to OHF-E-D3 with comparable apparent affinities to those observed to LGT-E-D3. The results for the OHF-E-D3 binding study are shown graphically in FIG. 2.

Example 5

Development of Peptide Libraries for Miniprotein Optimization

Studies directed toward optimizing the HPQ sequence of MP-100 using peptide mixture libraries have been carried out using the procedure which follows. A mixture of 18 MP-100C peptides was synthesized with the sequence RCCXPQCKEGKKCR (SEQ ID NO:179), where X represents all of the naturally occurring amino acids except Cys and Trp (XPQ library). Differential blocking group chemistry was used to prepare MP-100N and MP-100C analogs. The mixture was enriched by binding to immobilized LGT-E-D3 and POW-E-D3 and quickly eluted at pH 2. The starting library and the two enriched samples were examined using MALDI mass spectrometry. The total integrated signal for the 18 expected species was normalized to 1.0 for each sample. The level of enrichment was expressed as a ratio of enriched signal/library signal for each amino acid as shown in FIG. 3. Phe (F), Try (Y), and His (H) (the starting amino acid) were significantly enriched (with values >1.5). The LGT-E-D3 and POW-E-D3 differ by only seven residues in E-D3 and bind the miniproteins identically within experimental error. Thus, the similar selection of MP-100 analogs by the two E-D3s suggests that the method is able to select the tighter binding sequences. A similar experiment with a mixture of MP-100C analogs in a XAQ library yielded Met (M) and Ser (S) (data not shown).

Example 6

Antiviral Activity of MP-100

Figure 4:
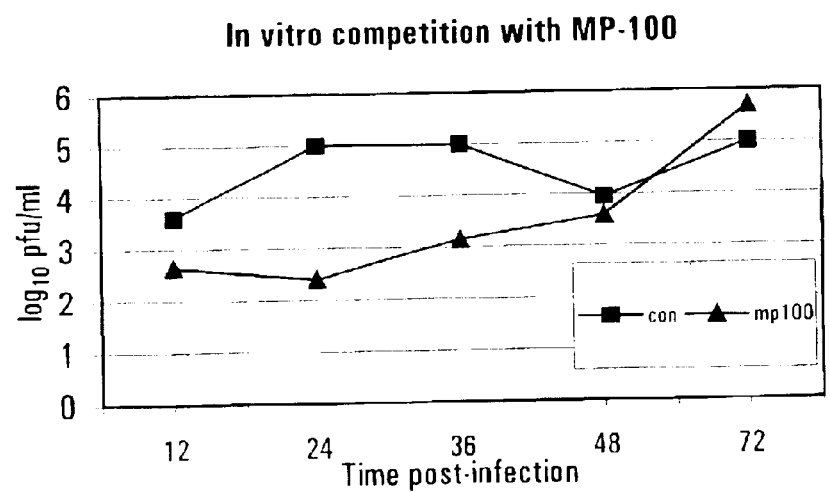
FIG. 4 is a graph showing in vitro protection from LGT virus infection using a polypeptide in accordance with the present invention.

Time course studies of MP-100 protection of Vero cells have yielded promising results. These assays were performed in Vero cells with MP-100 bound to virus using a concentration of 100 $\mu$M MP-100 prior to infection of cultured cells. MP-100 was not maintained in the culture medium during the experiment. The peptide MP-100 reduced viral titer by −300-fold at 24 hpi and −100-fold at 36 hpi, as shown in FIG. 4. These data indicate that a single dose of MP-100 delays the replication cycle of LGT virus.

Example 7

Toxicity Assays of Domain III and MP-100

Initial experiments using 100–150 $\mu$M LGT-E-D3 or MP-100 in female 3–4 week old NIH Swiss-mice indicate that neither of the agents is toxic to the mice at the dose administered. Agent was injected intravenously (iv) via the tail vein for five consecutive days (16.7 $\mu$g/day). Both agent treated and mock treated animals remained healthy throughout the 10-day course of observation.

Example 8

Mouse Protection by MP-100

Figure 5:
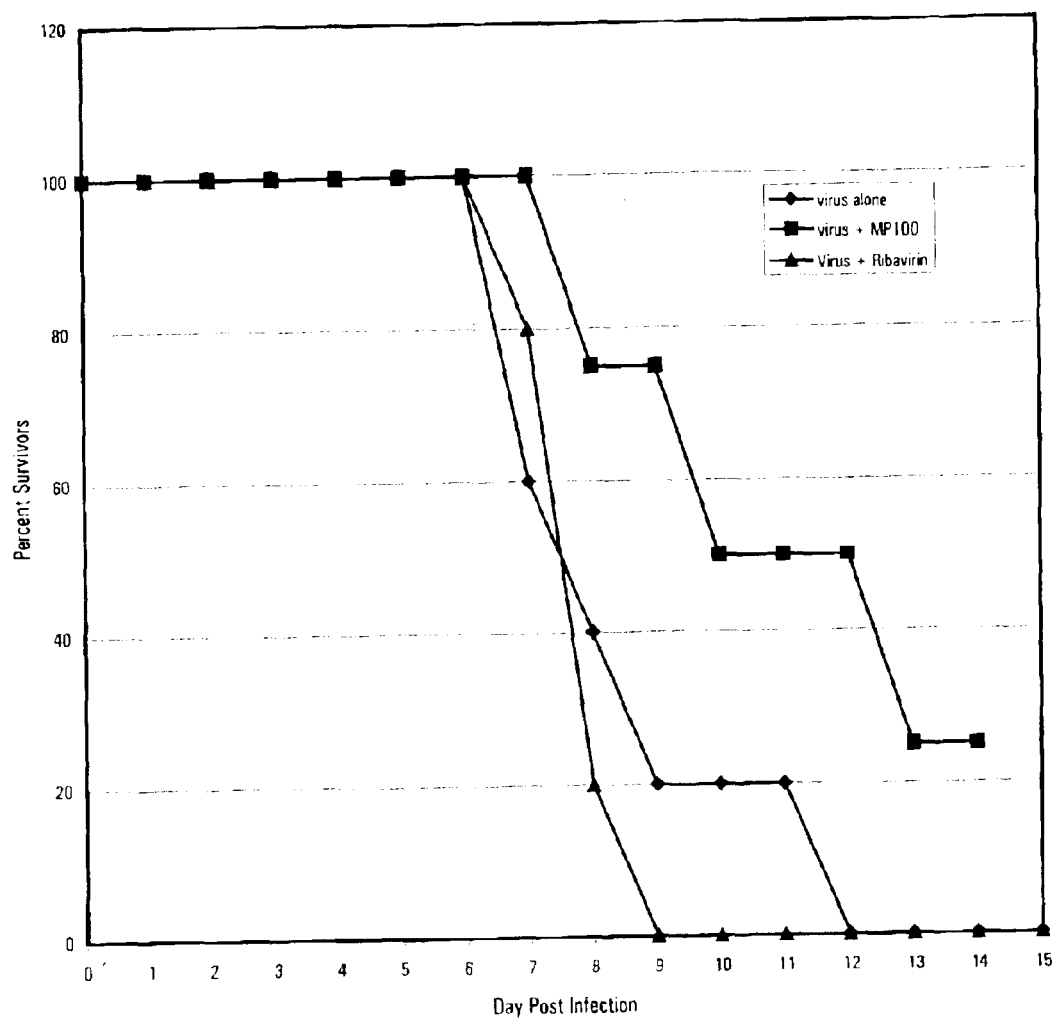
FIG. 5 is a graph showing in vivo protection of mice from LGT virus infection using a polypeptide in accordance with the present invention.

LGT virus is a good model for cell culture studies as it naturally attenuated and can be used at BSL-2. However, it is not neuroinvasive in mice and will only cause disease when inoculated directly in to the brain. In comparison, POW virus, a BSL-3 virus, is neuroinvasive and causes a lethal infection when inoculated by the intraperitoneal (ip) route. The binding of MP-100 to POW virus prior to ip viral challenge has demonstrated a delay in onset of disease in 5–6 week old female NIH Swiss mice. MP-100 was incubated with 3logLD$_{50}$ of POW virus prior to challenge via the ip route. Animals protected with a homogeneous solution of MP-100C remained healthy longer, and also survived longer, than control animals, as shown in FIG. 5 (♦, virus alone; ■, virus+MP-100; ▲, virus+ribavirin). MP-100N also showed some protection with an increase in long-term survival, though the animals did not show protection from onset of illness. These data suggest that the binding of MP-100 to virus elicits protection in an in vivo model. Pilot experiments examining the role of route of administration have also been performed with MP-100. Preliminary evidence suggests that i.v. administration of mice with MP-100 24 h prior to viral challenge increases their chance for survival (data not shown).

Example 9

Preparation of Miniprotein Ligands That Binds to LGT-E-D3 and OHF-E-D3

Using the phage display technique set forth in Example 4, above, the following additional sequences that bind to flavivirus Domain III's were identified. They are:

| MP-101 | RCCGYACKEGKNCR | (SEQ ID NO:158) |
| MP-102 | RCCVLACKEGKKCR | (SEQ ID NO:159) |
| MP-103 | RCCATVCKEGKKCR | (SEQ ID NO:160) |
| MP-104 | RCCELGCKEGKKCR | (SEQ ID NO:161) |
| MP-105 | RCCTAVCKEGKKCR | (SEQ ID NO:162) |
| MP-106 | RCCREPCKEGRKCR | (SEQ ID NO:163) |
| MP-107 | RCCVSVCKEGKKCR | (SEQ ID NO:164) |
| MP-108 | RCCTLRCKEGKKCR | (SEQ ID NO:165) |
| MP-109 | RCCVRQCKEGKKCR | (SEQ ID NO:166) |
| MP-110 | RCCTPTCKQGKKCR | (SEQ ID NO:167) |
| MP-111 | RCCEYDCKEGKKCR | (SEQ ID NO:168) |

MP-101, MP-102, and MP-105 were selected by binding to LGT-E-D3; MP-101 was selected by binding to POW-E-D3; MP-103, MP-104, MP-109, MP-110, and MP-111 were selected by binding to OHF-E-D3; and MP-106, MP-107, and MP-108 were selected by binding to WN-E-D3.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A polypeptide comprising an amino acid sequence of SEQ ID NO: 1, and wherein said polypeptide is capable of binding to a Domain III of a flavivirus.

2. A polypeptide according to claim 1, wherein said polypeptide comprises an amino acid sequence of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

3. A polypeptide according to claim 1, wherein said polypeptide comprises an amino acid sequence of SEQ ID NO: 14.

4. A polypeptide according to claim 1, wherein said polypeptide comprises an amino acid sequence of SEQ ID NO: 27.

5. A polypeptide according to claim 1, wherein said polypeptide comprises an amino acid sequence of SEQ ID NO: 40.

6. A polypeptide according to claim 1, wherein said polypeptide comprises an amino acid sequence of SEQ ID NO: 53.

7. A polypeptide according to claim 1, wherein said polypeptide comprises an amino acid sequence of SEQ ID NO: 66.

8. A polypeptide according to claim 1, wherein said polypeptide comprises an amino acid sequence of SEQ ID NO: 79.

9. A polypeptide according to claim 1, wherein said polypeptide comprises an amino acid sequence of SEQ ID NO: 92.

10. A polypeptide according to claim 1, wherein said polypeptide contains one or more disulfide bonds between non-adjacent cysteine amino acid residues.

11. A polypeptide according to claim 1, wherein said polypeptide is isolated.

12. A polypeptide according to claim 1, wherein said polypeptide is purified.

13. A polypeptide according to claim 1, wherein said polypeptide contains 12–1000 amino acids.

14. A polypeptide according to claim 1, wherein said polypeptide contains 12–25 amino acids.

15. A polypeptide according to claim 1, wherein said polypeptide comprises an amino acid sequence of SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, or SEQ ID NO: 168.

* * * * *

SEQUENCE LISTING

<160> NUMBER OF SEQ ID NOS: 180

<210> SEQ ID NO 1
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid
<220> FEATURE:
<221> NAME/KEY: MISC_FEATURE
<222> LOCATION: (10)..(11)
<223> OTHER INFORMATION: Xaa can be any amino acid

<400> SEQUENCE: 1

Cys Cys Xaa Xaa Xaa Cys Lys Glu Gly Xaa Xaa Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid

<400> SEQUENCE: 2

Cys Cys His Pro Gln Cys Lys Glu Gly Xaa Xaa Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid

<400> SEQUENCE: 3

Cys Cys Gly Tyr Ala Cys Lys Glu Gly Xaa Xaa Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid

<400> SEQUENCE: 4

Cys Cys Val Leu Ala Cys Lys Glu Gly Xaa Xaa Cys
1               5                   10

<210> SEQ ID NO 5
<211> LENGTH: 12

```
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 5

Cys Cys Ala Thr Val Cys Lys Glu Gly Xaa Xaa Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 6

Cys Cys Glu Leu Gly Cys Lys Glu Gly Xaa Xaa Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (10)..(11)
<223> OTHER INFORMATION: Xaa can be any amino acid.

<400> SEQUENCE: 7

Cys Cys Thr Ala Val Cys Lys Glu Gly Xaa Xaa Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 8

Cys Cys Arg Glu Pro Cys Lys Glu Gly Xaa Xaa Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 9
```

```
Cys Cys Val Ser Val Cys Lys Glu Gly Xaa Xaa Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 10

Cys Cys Thr Leu Arg Cys Lys Glu Gly Xaa Xaa Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 11

Cys Cys Val Arg Gln Cys Lys Glu Gly Xaa Xaa Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 12

Cys Cys Thr Pro Thr Cys Lys Glu Gly Xaa Xaa Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(11)
<223> OTHER INFORMATION: Xaa can be any amino acid.

<400> SEQUENCE: 13

Cys Cys Glu Tyr Asp Cys Lys Glu Gly Xaa Xaa Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Chemically synthesized
<220> FEATURE:
```

```
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (11)..(11)
<223> OTHER INFORMATION: Xaa can be any amino acid.

<400> SEQUENCE: 14

Cys Cys Xaa Xaa Xaa Cys Lys Glu Gly Lys Xaa Cys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 15

Cys Cys His Pro Gln Cys Lys Glu Gly Lys Xaa Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 16

Cys Cys Gly Tyr Ala Cys Lys Glu Gly Lys Xaa Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 17

Cys Cys Val Leu Ala Cys Lys Glu Gly Lys Xaa Cys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 18

Cys Cys Ala Thr Val Cys Lys Glu Gly Lys Xaa Cys
```

-continued

```
<210> SEQ ID NO 19
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 19

Cys Cys Glu Leu Gly Cys Lys Glu Gly Lys Xaa Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 20

Cys Cys Thr Ala Val Cys Lys Glu Gly Lys Xaa Cys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 21

Cys Cys Arg Glu Pro Cys Lys Glu Gly Lys Xaa Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 22

Cys Cys Val Ser Val Cys Lys Glu Gly Lys Xaa Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
```

```
<222> LOCATION: (11)..(11)
<223> OTHER INFORMATION: Xaa can be any amino acid.

<400> SEQUENCE: 23

Cys Cys Thr Leu Arg Cys Lys Glu Gly Lys Xaa Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 24

Cys Cys Val Arg Gln Cys Lys Glu Gly Lys Xaa Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 25

Cys Cys Thr Pro Thr Cys Lys Glu Gly Lys Xaa Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 26

Cys Cys Glu Tyr Asp Cys Lys Glu Gly Lys Xaa Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (10)..(10)
<223> OTHER INFORMATION: Xaa can be any amino acid.

<400> SEQUENCE: 27

Cys Cys Xaa Xaa Xaa Cys Lys Glu Gly Xaa Lys Cys
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 28

Cys Cys His Pro Gln Cys Lys Glu Gly Xaa Lys Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 29

Cys Cys Gly Tyr Ala Cys Lys Glu Gly Xaa Lys Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 30

Cys Cys Val Leu Ala Cys Lys Glu Gly Xaa Lys Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 31

Cys Cys Ala Thr Val Cys Lys Glu Gly Xaa Lys Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)

<223> OTHER INFORMATION: Xaa can be any amino acid.

<400> SEQUENCE: 32

Cys Cys Glu Leu Gly Cys Lys Glu Gly Xaa Lys Cys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 33

Cys Cys Thr Ala Val Cys Lys Glu Gly Xaa Lys Cys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 34

Cys Cys Arg Glu Pro Cys Lys Glu Gly Xaa Lys Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 35

Cys Cys Val Ser Val Cys Lys Glu Gly Xaa Lys Cys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 36

Cys Cys Thr Leu Arg Cys Lys Glu Gly Xaa Lys Cys
1               5                   10

<210> SEQ ID NO 37
<211> LENGTH: 12
<212> TYPE: PRT

```
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 37

Cys Cys Val Arg Gln Cys Lys Glu Gly Xaa Lys Cys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 38

Cys Cys Thr Pro Thr Cys Lys Glu Gly Xaa Lys Cys
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 39

Cys Cys Glu Tyr Asp Cys Lys Glu Gly Xaa Lys Cys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (10)..(10)
<223> OTHER INFORMATION: Xaa can be any amino acid.

<400> SEQUENCE: 40

Cys Cys Xaa Xaa Xaa Cys Lys Glu Gly Xaa Asn Cys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.
```

```
<400> SEQUENCE: 41

Cys Cys His Pro Gln Cys Lys Glu Gly Xaa Asn Cys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 42

Cys Cys Gly Tyr Ala Cys Lys Glu Gly Xaa Asn Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 43

Cys Cys Val Leu Ala Cys Lys Glu Gly Xaa Asn Cys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 44

Cys Cys Ala Thr Val Cys Lys Glu Gly Xaa Asn Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 45

Cys Cys Glu Leu Gly Cys Lys Glu Gly Xaa Asn Cys
1               5                   10

<210> SEQ ID NO 46
<211> LENGTH: 12
<212> TYPE: PRT
<213> ORGANISM: Artificial Sequence
```

```
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 46

Cys Cys Thr Ala Val Cys Lys Glu Gly Xaa Asn Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 47

Cys Cys Arg Glu Pro Cys Lys Glu Gly Xaa Asn Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 48

Cys Cys Val Ser Val Cys Lys Glu Gly Xaa Asn Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 49

Cys Cys Thr Leu Arg Cys Lys Glu Gly Xaa Asn Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 50

Cys Cys Val Arg Gln Cys Lys Glu Gly Xaa Asn Cys
1               5                   10
```

<210> SEQ ID NO 51
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 51

Cys Cys Thr Pro Thr Cys Lys Glu Gly Xaa Asn Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa can be any amino acid.

<400> SEQUENCE: 52

Cys Cys Glu Tyr Asp Cys Lys Glu Gly Xaa Asn Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (11)..(11)
<223> OTHER INFORMATION: Xaa can be any amino acid.

<400> SEQUENCE: 53

Cys Cys Xaa Xaa Xaa Cys Lys Glu Gly Arg Xaa Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 54

Cys Cys His Pro Gln Cys Lys Glu Gly Arg Xaa Cys
1               5                   10

<210> SEQ ID NO 55
<211> LENGTH: 12
<212> TYPE: PRT
<213> ORGANISM: Artificial Sequence
<220> FEATURE:

```
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 55

Cys Cys Gly Tyr Ala Cys Lys Glu Gly Arg Xaa Cys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 56

Cys Cys Val Leu Ala Cys Lys Glu Gly Arg Xaa Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 57

Cys Cys Ala Thr Val Cys Lys Glu Gly Arg Xaa Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 58

Cys Cys Glu Leu Gly Cys Lys Glu Gly Arg Xaa Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 59

Cys Cys Thr Ala Val Cys Lys Glu Gly Arg Xaa Cys
1               5                   10
```

```
<210> SEQ ID NO 60
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 60

Cys Cys Arg Glu Pro Cys Lys Glu Gly Arg Xaa Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 61

Cys Cys Val Ser Val Cys Lys Glu Gly Arg Xaa Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 62

Cys Cys Thr Leu Arg Cys Lys Glu Gly Arg Xaa Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 63

Cys Cys Val Arg Gln Cys Lys Glu Gly Arg Xaa Cys
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.
```

```
<400> SEQUENCE: 64

Cys Cys Thr Pro Thr Cys Lys Glu Gly Arg Xaa Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa can be any amino acid.

<400> SEQUENCE: 65

Cys Cys Glu Tyr Asp Cys Lys Glu Gly Arg Xaa Cys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.

<400> SEQUENCE: 66

Cys Cys Xaa Xaa Xaa Cys Lys Glu Gly Lys Lys Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Chemically synthesized

<400> SEQUENCE: 67

Cys Cys His Pro Gln Cys Lys Glu Gly Lys Lys Cys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Chemically synthesized

<400> SEQUENCE: 68

Cys Cys Gly Tyr Ala Cys Lys Glu Gly Lys Lys Cys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Chemically synthesized

<400> SEQUENCE: 69

Cys Cys Val Leu Ala Cys Lys Glu Gly Lys Lys Cys
1               5                   10
```

```
<210> SEQ ID NO 70
<211> LENGTH: 12
<212> TYPE: PRT
<213> ORGANISM: Artificial Sequence
<220> FEATURE:
<223> OTHER INFORMATION: Chemically synthesized

<400> SEQUENCE: 70

Cys Cys Ala Thr Val Cys Lys Glu Gly Lys Lys Cys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Chemically synthesized

<400> SEQUENCE: 71

Cys Cys Glu Leu Gly Cys Lys Glu Gly Lys Lys Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Chemically synthesized

<400> SEQUENCE: 72

Cys Cys Thr Ala Val Cys Lys Glu Gly Lys Lys Cys
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Chemically synthesized

<400> SEQUENCE: 73

Cys Cys Arg Glu Pro Cys Lys Glu Gly Lys Lys Cys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Chemically synthesized

<400> SEQUENCE: 74

Cys Cys Val Ser Val Cys Lys Glu Gly Lys Lys Cys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Chemically synthesized

<400> SEQUENCE: 75

Cys Cys Thr Leu Arg Cys Lys Glu Gly Lys Lys Cys
1               5                   10
```

```
<210> SEQ ID NO 76
<211> LENGTH: 12
<212> TYPE: PRT
<213> ORGANISM: Artificial Sequence
<220> FEATURE:
<223> OTHER INFORMATION: Chemically synthesized

<400> SEQUENCE: 76

Cys Cys Val Arg Gln Cys Lys Glu Gly Lys Lys Cys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Chemically synthesized

<400> SEQUENCE: 77

Cys Cys Thr Pro Thr Cys Lys Glu Gly Lys Lys Cys
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Chemically synthesized

<400> SEQUENCE: 78

Cys Cys Glu Tyr Asp Cys Lys Glu Gly Lys Lys Cys
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.

<400> SEQUENCE: 79

Cys Cys Xaa Xaa Xaa Cys Lys Glu Gly Lys Asn Cys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Chemically synthesized

<400> SEQUENCE: 80

Cys Cys His Pro Gln Cys Lys Glu Gly Lys Asn Cys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Chemically synthesized

<400> SEQUENCE: 81

Cys Cys Gly Tyr Ala Cys Lys Glu Gly Lys Asn Cys
```

```
<210> SEQ ID NO 82
<211> LENGTH: 12
<212> TYPE: PRT
<213> ORGANISM: Artificial Sequence
<220> FEATURE:
<223> OTHER INFORMATION: Chemically synthesized

<400> SEQUENCE: 82

Cys Cys Val Leu Ala Cys Lys Glu Gly Lys Asn Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Chemically synthesized

<400> SEQUENCE: 83

Cys Cys Ala Thr Val Cys Lys Glu Gly Lys Asn Cys
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Chemically synthesized

<400> SEQUENCE: 84

Cys Cys Glu Leu Gly Cys Lys Glu Gly Lys Asn Cys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Chemically synthesized

<400> SEQUENCE: 85

Cys Cys Thr Ala Val Cys Lys Glu Gly Lys Asn Cys
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Chemically synthesized

<400> SEQUENCE: 86

Cys Cys Arg Glu Pro Cys Lys Glu Gly Lys Asn Cys
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Chemically synthesized

<400> SEQUENCE: 87

Cys Cys Val Ser Val Cys Lys Glu Gly Lys Asn Cys
1               5                   10
```

<210> SEQ ID NO 88
<211> LENGTH: 12
<212> TYPE: PRT
<213> ORGANISM: Artificial Sequence
<220> FEATURE:
<223> OTHER INFORMATION: Chemically synthesized

<400> SEQUENCE: 88

Cys Cys Thr Leu Arg Cys Lys Glu Gly Lys Asn Cys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Chemically synthesized

<400> SEQUENCE: 89

Cys Cys Val Arg Gln Cys Lys Glu Gly Lys Asn Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Chemically synthesized

<400> SEQUENCE: 90

Cys Cys Thr Pro Thr Cys Lys Glu Gly Lys Asn Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Chemically synthesized

<400> SEQUENCE: 91

Cys Cys Glu Tyr Asp Cys Lys Glu Gly Lys Asn Cys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.

<400> SEQUENCE: 92

Cys Cys Xaa Xaa Xaa Cys Lys Glu Gly Arg Lys Cys
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Chemically synthesized

<400> SEQUENCE: 93

Cys Cys His Pro Gln Cys Lys Glu Gly Arg Lys Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Chemically synthesized

<400> SEQUENCE: 94

Cys Cys Gly Tyr Ala Cys Lys Glu Gly Arg Lys Cys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Chemically synthesized

<400> SEQUENCE: 95

Cys Cys Val Leu Ala Cys Lys Glu Gly Arg Lys Cys
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Chemically synthesized

<400> SEQUENCE: 96

Cys Cys Ala Thr Val Cys Lys Glu Gly Arg Lys Cys
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Chemically synthesized

<400> SEQUENCE: 97

Cys Cys Glu Leu Gly Cys Lys Glu Gly Arg Lys Cys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Chemically synthesized

<400> SEQUENCE: 98

Cys Cys Thr Ala Val Cys Lys Glu Gly Arg Lys Cys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Chemically synthesized

<400> SEQUENCE: 99

```
Cys Cys Arg Glu Pro Cys Lys Glu Gly Arg Lys Cys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Chemically synthesized

<400> SEQUENCE: 100

Cys Cys Val Ser Val Cys Lys Glu Gly Arg Lys Cys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Chemically synthesized

<400> SEQUENCE: 101

Cys Cys Thr Leu Arg Cys Lys Glu Gly Arg Lys Cys
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Chemically synthesized

<400> SEQUENCE: 102

Cys Cys Val Arg Gln Cys Lys Glu Gly Arg Lys Cys
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Chemically synthesized

<400> SEQUENCE: 103

Cys Cys Thr Pro Thr Cys Lys Glu Gly Arg Lys Cys
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Chemically synthesized

<400> SEQUENCE: 104

Cys Cys Glu Tyr Asp Cys Lys Glu Gly Arg Lys Cys
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
```

```
<220> FEATURE:
<221> NAME/KEY: MISC_FEATURE
<222> LOCATION: (7)..(7)
<223> OTHER INFORMATION: Xaa can be any amino acid.

<400> SEQUENCE: 105

Cys Cys Xaa Xaa Xaa Cys Xaa Glu Gly Lys Lys Cys
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (8)..(8)
<223> OTHER INFORMATION: Xaa can be any amino acid.

<400> SEQUENCE: 106

Cys Cys Xaa Xaa Xaa Cys Lys Xaa Gly Lys Lys Cys
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (9)..(9)
<223> OTHER INFORMATION: Xaa can be any amino acid.

<400> SEQUENCE: 107

Cys Cys Xaa Xaa Xaa Cys Lys Glu Xaa Lys Lys Cys
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (7)..(7)
<223> OTHER INFORMATION: Xaa can be any amino acid.

<400> SEQUENCE: 108

Cys Cys Xaa Xaa Xaa Cys Xaa Glu Gly Lys Asn Cys
1               5                   10

<210> SEQ ID NO 109
<211> LENGTH: 12
<212> TYPE: PRT
<213> ORGANISM: Artificial Sequence
<220> FEATURE:
```

```
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (8)..(8)
<223> OTHER INFORMATION: Xaa can be any amino acid.

<400> SEQUENCE: 109

Cys Cys Xaa Xaa Xaa Cys Lys Xaa Gly Lys Asn Cys
 1               5                  10

<210> SEQ ID NO 110
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (9)..(9)
<223> OTHER INFORMATION: Xaa can be any amino acid.

<400> SEQUENCE: 110

Cys Cys Xaa Xaa Xaa Cys Lys Glu Xaa Lys Asn Cys
 1               5                  10

<210> SEQ ID NO 111
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (7)..(7)
<223> OTHER INFORMATION: Xaa can be any amino acid.

<400> SEQUENCE: 111

Cys Cys Xaa Xaa Xaa Cys Xaa Glu Gly Arg Lys Cys
 1               5                  10

<210> SEQ ID NO 112
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (8)..(8)
<223> OTHER INFORMATION: Xaa can be any amino acid.

<400> SEQUENCE: 112

Cys Cys Xaa Xaa Xaa Cys Lys Xaa Gly Arg Lys Cys
 1               5                  10
```

```
<210> SEQ ID NO 113
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (9)..(9)
<223> OTHER INFORMATION: Xaa can be any amino acid.

<400> SEQUENCE: 113

Cys Cys Xaa Xaa Xaa Cys Lys Glu Xaa Arg Lys Cys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 114

Cys Cys His Pro Gln Cys Xaa Glu Gly Lys Lys Cys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 115

Cys Cys Gly Tyr Ala Cys Xaa Glu Gly Lys Asn Cys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 116

Cys Cys Val Leu Ala Cys Xaa Glu Gly Lys Lys Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Chemically synthesized
<220> FEATURE:
```

```
<221> NAME/KEY: MISC_FEATURE
<222> LOCATION: (7)..(7)
<223> OTHER INFORMATION: Xaa can be any amino acid.

<400> SEQUENCE: 117

Cys Cys Ala Thr Val Cys Xaa Glu Gly Lys Lys Cys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 118

Cys Cys Glu Leu Gly Cys Xaa Glu Gly Lys Lys Cys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 119

Cys Cys Thr Ala Val Cys Xaa Glu Gly Lys Lys Cys
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 120

Cys Cys Arg Glu Pro Cys Xaa Glu Gly Arg Lys Cys
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 121

Cys Cys Val Ser Val Cys Xaa Glu Gly Lys Lys Cys
1               5                   10

<210> SEQ ID NO 122
```

```
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 122

Cys Cys Thr Leu Arg Cys Xaa Glu Gly Lys Lys Cys
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 123

Cys Cys Val Arg Gln Cys Xaa Glu Gly Lys Lys Cys
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 124

Cys Cys Thr Pro Thr Cys Xaa Glu Gly Lys Lys Cys
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa can be any amino acid.

<400> SEQUENCE: 125

Cys Cys Glu Tyr Asp Cys Xaa Glu Gly Lys Lys Cys
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 126
```

Cys Cys His Pro Gln Cys Lys Xaa Gly Lys Lys Cys
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 127

Cys Cys Gly Tyr Ala Cys Lys Xaa Gly Lys Asn Cys
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 128

Cys Cys Val Leu Ala Cys Lys Xaa Gly Lys Lys Cys
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 129

Cys Cys Ala Thr Val Cys Lys Xaa Gly Lys Lys Cys
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 130

Cys Cys Glu Leu Gly Cys Lys Xaa Gly Lys Lys Cys
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Chemically synthesized

```
<220> FEATURE:
<221> NAME/KEY: MISC_FEATURE
<222> LOCATION: (8)..(8)
<223> OTHER INFORMATION: Xaa can be any amino acid.

<400> SEQUENCE: 131

Cys Cys Thr Ala Val Cys Lys Xaa Gly Lys Lys Cys
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 132

Cys Cys Arg Glu Pro Cys Lys Xaa Gly Arg Lys Cys
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 133

Cys Cys Val Ser Val Cys Lys Xaa Gly Lys Lys Cys
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 134

Cys Cys Thr Leu Arg Cys Lys Xaa Gly Lys Lys Cys
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 135

Cys Cys Val Arg Gln Cys Lys Xaa Gly Lys Lys Cys
1               5                   10
```

```
<210> SEQ ID NO 136
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 136

Cys Cys Thr Pro Thr Cys Lys Xaa Gly Lys Lys Cys
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa can be any amino acid.

<400> SEQUENCE: 137

Cys Cys Glu Tyr Asp Cys Lys Xaa Gly Lys Lys Cys
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 138

Cys Cys His Pro Gln Cys Lys Glu Xaa Lys Lys Cys
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 139

Cys Cys Gly Tyr Ala Cys Lys Glu Xaa Lys Asn Cys
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.
```

```
<400> SEQUENCE: 140

Cys Cys Val Leu Ala Cys Lys Glu Xaa Lys Lys Cys
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 141

Cys Cys Ala Thr Val Cys Lys Glu Xaa Lys Lys Cys
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 142

Cys Cys Glu Leu Gly Cys Lys Glu Xaa Lys Lys Cys
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 143

Cys Cys Thr Ala Val Cys Lys Glu Xaa Lys Lys Cys
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 144

Cys Cys Arg Glu Pro Cys Lys Glu Xaa Arg Lys Cys
1               5                   10

<210> SEQ ID NO 145
<211> LENGTH: 12
<212> TYPE: PRT
<213> ORGANISM: Artificial Sequence
<220> FEATURE:
```

```
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 145

Cys Cys Val Ser Val Cys Lys Glu Xaa Lys Lys Cys
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 146

Cys Cys Thr Leu Arg Cys Lys Glu Xaa Lys Lys Cys
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 147

Cys Cys Val Arg Gln Cys Lys Glu Xaa Lys Lys Cys
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 148

Cys Cys Thr Pro Thr Cys Lys Glu Xaa Lys Lys Cys
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (9)..(9)
<223> OTHER INFORMATION: Xaa can be any amino acid.

<400> SEQUENCE: 149

Cys Cys Glu Tyr Asp Cys Lys Glu Xaa Lys Lys Cys
1               5                   10
```

```
<210> SEQ ID NO 150
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (11)..(12)
<223> OTHER INFORMATION: Xaa can be any amino acid.

<400> SEQUENCE: 150

Arg Cys Cys Xaa Xaa Xaa Cys Lys Glu Gly Xaa Xaa Cys Arg
 1               5                  10

<210> SEQ ID NO 151
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (12)..(12)
<223> OTHER INFORMATION: Xaa can be any amino acid.

<400> SEQUENCE: 151

Arg Cys Cys Xaa Xaa Xaa Cys Lys Glu Gly Lys Xaa Cys Arg
 1               5                  10

<210> SEQ ID NO 152
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (12)..(12)
<223> OTHER INFORMATION: Xaa can be any amino acid.

<400> SEQUENCE: 152

Arg Cys Cys Xaa Xaa Xaa Cys Lys Glu Gly Arg Xaa Cys Arg
 1               5                  10

<210> SEQ ID NO 153
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (11)..(11)
<223> OTHER INFORMATION: Xaa can be any amino acid.
```

-continued

```
<400> SEQUENCE: 153

Arg Cys Cys Xaa Xaa Xaa Cys Lys Glu Gly Xaa Asn Cys Arg
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.

<400> SEQUENCE: 154

Arg Cys Cys Xaa Xaa Xaa Cys Lys Glu Gly Lys Lys Cys Arg
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.

<400> SEQUENCE: 155

Arg Cys Cys Xaa Xaa Xaa Cys Lys Glu Gly Arg Lys Cys Arg
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.

<400> SEQUENCE: 156

Arg Cys Cys Xaa Xaa Xaa Cys Lys Glu Gly Lys Asn Cys Arg
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Chemically synthesized

<400> SEQUENCE: 157

Arg Cys Cys His Pro Gln Cys Lys Glu Gly Lys Lys Cys Arg
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Chemically synthesized

<400> SEQUENCE: 158
```

```
Arg Cys Cys Gly Tyr Ala Cys Lys Glu Gly Lys Asn Cys Arg
1               5                   10
```

<210> SEQ ID NO 159
<211> LENGTH: 14
<212> TYPE: PRT
<213> ORGANISM: Artificial Sequence
<220> FEATURE:
<223> OTHER INFORMATION: Chemically synthesized

<400> SEQUENCE: 159

```
Arg Cys Cys Val Leu Ala Cys Lys Glu Gly Lys Lys Cys Arg
1               5                   10
```

<210> SEQ ID NO 160
<211> LENGTH: 14
<212> TYPE: PRT
<213> ORGANISM: Artificial Sequence
<220> FEATURE:
<223> OTHER INFORMATION: Chemically synthesized

<400> SEQUENCE: 160

```
Arg Cys Cys Ala Thr Val Cys Lys Glu Gly Lys Lys Cys Arg
1               5                   10
```

<210> SEQ ID NO 161
<211> LENGTH: 14
<212> TYPE: PRT
<213> ORGANISM: Artificial Sequence
<220> FEATURE:
<223> OTHER INFORMATION: Chemically synthesized

<400> SEQUENCE: 161

```
Arg Cys Cys Glu Leu Gly Cys Lys Glu Gly Lys Lys Cys Arg
1               5                   10
```

<210> SEQ ID NO 162
<211> LENGTH: 14
<212> TYPE: PRT
<213> ORGANISM: Artificial Sequence
<220> FEATURE:
<223> OTHER INFORMATION: Chemically synthesized

<400> SEQUENCE: 162

```
Arg Cys Cys Thr Ala Val Cys Lys Glu Gly Lys Lys Cys Arg
1               5                   10
```

<210> SEQ ID NO 163
<211> LENGTH: 14
<212> TYPE: PRT
<213> ORGANISM: Artificial Sequence
<220> FEATURE:
<223> OTHER INFORMATION: Chemically synthesized

<400> SEQUENCE: 163

```
Arg Cys Cys Arg Glu Pro Cys Lys Glu Gly Arg Lys Cys Arg
1               5                   10
```

<210> SEQ ID NO 164
<211> LENGTH: 14
<212> TYPE: PRT
<213> ORGANISM: Artificial Sequence
<220> FEATURE:
<223> OTHER INFORMATION: Chemically synthesized

<400> SEQUENCE: 164

```
Arg Cys Cys Val Ser Val Cys Lys Glu Gly Lys Lys Cys Arg
```

-continued

```
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Chemically synthesized

<400> SEQUENCE: 165

Arg Cys Cys Thr Leu Arg Cys Lys Glu Gly Lys Lys Cys Arg
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Chemically synthesized

<400> SEQUENCE: 166

Arg Cys Cys Val Arg Gln Cys Lys Glu Gly Lys Lys Cys Arg
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Chemically synthesized

<400> SEQUENCE: 167

Arg Cys Cys Thr Pro Thr Cys Lys Glu Gly Lys Lys Cys Arg
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Chemically synthesized

<400> SEQUENCE: 168

Arg Cys Cys Glu Tyr Asp Cys Lys Glu Gly Lys Lys Cys Arg
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Chemically synthesized

<400> SEQUENCE: 169

Cys Cys Thr Pro Thr Cys Lys Gln Gly Lys Lys Cys
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Chemically synthesized

<400> SEQUENCE: 170

Arg Cys Cys Thr Pro Thr Cys Lys Gln Gly Lys Lys Cys Arg
1               5                   10
```

```
<210> SEQ ID NO 171
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(5)
<223> OTHER INFORMATION: Xaa can be any amino acid.
<220> FEATURE:
<221> NAME/KEY: MISC_FEATURE
<222> LOCATION: (7)..(11)
<223> OTHER INFORMATION: Xaa can be any amino acid.

<400> SEQUENCE: 171

Cys Cys Xaa Xaa Xaa Cys Xaa Xaa Xaa Xaa Xaa Cys
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (8)..(12)
<223> OTHER INFORMATION: Xaa can be any amino acid.

<400> SEQUENCE: 172

Arg Cys Cys Xaa Xaa Xaa Cys Xaa Xaa Xaa Xaa Xaa Cys Arg
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (8)..(11)
<223> OTHER INFORMATION: Xaa can be any amino acid.

<400> SEQUENCE: 173

Arg Cys Cys Xaa Xaa Xaa Cys Xaa Xaa Xaa Xaa Cys Arg
1               5                   10

<210> SEQ ID NO 174
<211> LENGTH: 15
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(6)
<223> OTHER INFORMATION: Xaa can be any amino acid.
<220> FEATURE:
<221> NAME/KEY: MISC_FEATURE
<222> LOCATION: (8)..(13)
<223> OTHER INFORMATION: Xaa can be any amino acid.
```

<400> SEQUENCE: 174

Arg Cys Cys Xaa Xaa Xaa Cys Xaa Xaa Xaa Xaa Xaa Xaa Cys Arg
1               5                   10                  15

<210> SEQ ID NO 175
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(7)
<223> OTHER INFORMATION: Xaa can be any amino acid.
<220> FEATURE:
<221> NAME/KEY: MISC_FEATURE
<222> LOCATION: (9)..(12)
<223> OTHER INFORMATION: Xaa can be any amino acid.

<400> SEQUENCE: 175

Arg Cys Cys Xaa Xaa Xaa Xaa Cys Xaa Xaa Xaa Xaa Cys Arg
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(7)
<223> OTHER INFORMATION: Xaa can be any amino acid.
<220> FEATURE:
<221> NAME/KEY: MISC_FEATURE
<222> LOCATION: (9)..(13)
<223> OTHER INFORMATION: Xaa can be any amino acid.

<400> SEQUENCE: 176

Arg Cys Cys Xaa Xaa Xaa Xaa Cys Xaa Xaa Xaa Xaa Xaa Cys Arg
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(8)
<223> OTHER INFORMATION: Xaa can be any amino acid.
<220> FEATURE:
<221> NAME/KEY: MISC_FEATURE
<222> LOCATION: (10)..(14)
<223> OTHER INFORMATION: Xaa can be any amino acid.

<400> SEQUENCE: 177

Arg Cys Cys Xaa Xaa Xaa Xaa Xaa Cys Xaa Xaa Xaa Xaa Xaa Cys Arg
1               5                   10                  15

<210> SEQ ID NO 178
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(12)

-continued

```
<223> OTHER INFORMATION: Xaa can be any amino acid.

<400> SEQUENCE: 178

Arg Cys Cys His Pro Gln Cys Xaa Xaa Xaa Xaa Xaa Cys Arg
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa can be any amino acid.

<400> SEQUENCE: 179

Arg Cys Cys Xaa Pro Gln Cys Lys Glu Gly Lys Lys Cys Arg
1               5                   10

<210> SEQ ID NO 180
<211> LENGTH: 13
<212> TYPE: PRT
<213> ORGANISM: Conus sp.

<400> SEQUENCE: 180

Glu Cys Cys Asn Pro Ala Cys Gly Arg His Tyr Ser Cys
1               5                   10
```